(12) United States Patent
Zhang

(10) Patent No.: US 8,426,373 B2
(45) Date of Patent: Apr. 23, 2013

(54) STABLE PHARMACEUTICAL COMPOSITION COMPRISING BETA-LACTAM ANTIBIOTIC AND ION-CHELATING AGENT

(76) Inventor: Hesheng Zhang, Tianjin (CN)

( * ) Notice: Subject to any disclaimer, the term of this patent is extended or adjusted under 35 U.S.C. 154(b) by 633 days.

(21) Appl. No.: 12/392,086

(22) Filed: Feb. 24, 2009

(65) Prior Publication Data
US 2009/0155387 A1 Jun. 18, 2009

Related U.S. Application Data

(63) Continuation of application No. PCT/CN2007/002438, filed on Aug. 14, 2007.

(30) Foreign Application Priority Data

Aug. 25, 2006 (CN) .......................... 2006 1 0015437

(51) Int. Cl.
*A61K 31/70* (2006.01)
(52) U.S. Cl.
USPC .............................. 514/36; 514/41; 514/192

(58) Field of Classification Search .................... 514/36, 514/41, 192
See application file for complete search history.

(56) References Cited

U.S. PATENT DOCUMENTS

| | | | | |
|---|---|---|---|---|
| 5,998,381 A | * | 12/1999 | Shekhani et al. | 514/25 |
| 6,007,810 A | * | 12/1999 | Ishikawa et al. | 424/94.62 |
| 6,900,184 B2 | * | 5/2005 | Cohen et al. | 514/36 |

FOREIGN PATENT DOCUMENTS

WO WO-2006/059344 A1 * 6/2006

OTHER PUBLICATIONS

Crosby et al., "Activity of Cefoperazone and Two β-Lactamase Inhibitors, Sulbactam and Clavulanic Acid, Against *Bacteroides* spp. Correlated with β-Lactamase Production", Sep. 1982, Antimicrobial Agents and Chemotherapy, vol. 22 No. 3, pp. 398-405.*

* cited by examiner

*Primary Examiner* — Ali Soroush
(74) *Attorney, Agent, or Firm* — Matthias Scholl P.C.; Matthias Scholl

(57) ABSTRACT

A pharmaceutical composition containing at least one β-lactam antibiotic, at least one ion-chelating agent, at least one buffer component, and at least one aminoglycoside antibiotic.

19 Claims, No Drawings

STABLE PHARMACEUTICAL COMPOSITION COMPRISING BETA-LACTAM ANTIBIOTIC AND ION-CHELATING AGENT

CROSS-REFERENCE TO RELATED APPLICATIONS

This application is a continuation of International Patent Application No. PCT/CN2007/002438, with an international filing date of Aug. 14, 2007, designating the US, now pending, which is based on Chinese Patent Application No. 200610015437.8, filed Aug. 25, 2006. The contents of these specifications are incorporated herein by reference.

BACKGROUND OF THE INVENTION

1. Field of the Invention

This invention relates to a pharmaceutical composition comprising at least a lactam antibiotic and at least an ion-chelating agent, which inhibits the formation of aggregates in the composition. Optionally, the pharmaceutical composition further comprises at least a β-lactamase inhibitor, or a buffer component, or at least a β-lactamase inhibitor and a buffer component. The pharmaceutical composition of the invention is stable in liquid form.

2. Description of the Related Art

Cephalosporins are derived from Cephalosporium bacteria. Among them, Cephalosprorin C is widely used due to its broad anti-bacterial spectrum and low toxicity. First, second, third, and fourth generations of semi-synthetic-β-lactam antibiotics have been developed though structure transformation of Cephalosprorin C. To date, β-lactam antibiotics account for about a half of all antibiotics used to fight microbial infections.

β-Lactam antibiotics inhibit the synthesis of bacteria cell wall by inhibiting the activity of the D-alanyl-D-alanine transpeptidase (peptidoglycan transpeptidase) inside bacteria. Peptidoglycans are linear polysaccharide polypeptides with a network structure alternately comprising N-acetylglucosamine (Glc-NAc) and Mur-NAc. The transpeptide cross-linking reaction of these linear polymers catalysed by peptidoglycan transpeptidase results in network architecture and completes cell wall synthesis. β-Lactam antibiotics irreversibly inhibit the activity of the peptidoglycan transpeptidase and cause a failure of bacterial cell wall formation. Without cell wall, bacterial cells don't have a definite shape and sustain high permeation pressure inside cells, which causes bacteriolysis resulting in the death of bacteria.

Bacteria have subsequently evolved to produce β-lactamase, which can hydrolyze the amido bond of the β-lactam ring of β-lactam antibiotics and transform β-lactam antibiotics into metabolites lacking antibacterial activity. In 1976, it was discovered that clavulanic acid separated from the fermented fluid of rod-like streptomycete was a unique β-lactamase inhibitor. Soon thereafter, other β-lactamase inhibitors, especially sulbactam and its lipid prodrugs, i.e., composition of ampicillin sodium and sulbactam sodium, and tazobactam became widely used in clinical settings.

Another type of antibiotics widely used is aminoglycoside antibiotics. Aminoglycoside antibiotics are glycosides formed from aminosugar (monosaccharide or disaccharide) and amino-cyclitol. They are alkaline in nature owing to their amino and other basic functional groups. Due to their broad anti-bacterial spectrum, high anti-bacterial activity, frequent clinical use, there have been more than 20 species of aminoglycosides developed since the discovery of the first aminoglycoside antibiotic, streptomycin, which was isulated from Streptothrix in 1940.

The anti-bacterial mechanism of action of aminoglycoside antibiotics is entirely different from that of β-lactam antibiotics. After entering bacteria the aminoglycoside antibiotic conjugates with the 30S subunit protein, which causes errors when tRNA translates mRNA code and results in non-functioning proteins inhibiting cell growth.

It is generally known that the combination of β-lactam antibiotics with aminoglycoside antibiotics provides an anti-bacterial synergy. However, β-lactam antibiotics are acidic whereas aminoglycoside antibiotics are basic. When these two types of antibiotics are dissolved in the same solution, either a salt precipitates out due to acid-base reaction, or the amino group of the aminoglycoside antibiotic reacts with the β-lactam group of the β-lactam antibiotics. Both of the reactions drastically reduce the efficacy of these types of antibiotics. Therefore, mixing of these two types of antibiotics in the same solution is normally disadvantageous.

A solution preparation of β-lactam antibiotics is not stable at room temperature. The solution forms aggregate particles, especially when a frozen preserved β-lactam antibiotics solution is thawed, or when a lyophilized powder preparation of β-lactam antibiotics is re-dissolved. In addition, the longer the solution stands, the more aggregate particles are generated. Aggregate particles in intravenous solution are harmful to the patient. Specifically, it has been found that infusion phlebitis is closely related to aggregate particle content in the infusion fluid (Remmington's Pharmaceutical Science, 18th Edition, Mark Publishing, 1990, p. 1567).

Further research has shown that when β-lactam antibiotics and aminoglycoside antibiotics are mixed in one solution, aggregate particles are more likely to occur. This has become another clinical problem that needs to be solved. A pharmaceutical composition, in which β-lactam antibiotics and aminoglycoside antibiotics can be stabilized while maintaining efficacy would be particularly beneficial in clinical use. Moreover, when a β-lactam antibiotic and an aminoglycoside antibiotic are combined in a mixture, the synergic bactericidal action can be achieved. This would have great social-economic significance.

SUMMARY OF THE INVENTION

In view of the above-described problems, it is one objective of the invention to provide a pharmaceutical composition which can be used as an anti-microbial and anti-infection drug.

In order to achieve the above objectives, in accordance with one embodiment of the invention, provided is a pharmaceutical compositon, comprising: at least one β-lactam antibiotic and at least one ion chelating reagent, which can prevent aggregate particle formation. In another embodiment, provided is a pharmaceutical compositon, comprising: at least one β-lactam antibiotic and at least one ion chelating reagent, which can prevent aggregate particle formation, and a buffer component.

The key in the development of a pharmaceutical composition of β-lactam antibiotics and aminoglycoside antibiotics which can be stabilized in one solution with maintained efficacy is finding an agent which would promote solubility of β-lactam antibiotics and aminoglycoside antibiotics, yet also inhibit a reaction between the β-lactam group of β-lactam antibiotics and the amino group of aminoglycoside antibiotics.

As a result of systematic studies, it has been found that when the pH value is controlled in the range of between 3 and 9, a precipitate resulting from salt forming reaction and the reaction between the β-lactam group of β-lactam antibiotics with the amino group of aminoglycoside antibiotics can be inhibited to a certain extent. When the pH value is controlled in the range of between 4 and 8, the precipitate and the reaction between the amino group and β-lactam can be inhibited to a significant degree. And, when the pH value is controlled in the range of 6-7.5, the precipitate and the reaction between the amino group and β-lactam group can be practically completely inhibited. Strong ion chelating reagents can further inhibit the above-mentioned reactions between β-lactam antibiotics and aminoglycoside antibiotics.

When the pharmaceutical composition is provided as a lyophilized powder and is dissolved in sterile water, clear and transparent solution is obtained, no turbidity or precipitate forms, and the efficacy of β-lactam antibiotic in the composition is maintained for at least 8 hours.

In a class of any embodiment of this invention, the composition is provided as a mixture with at least an aminoglycoside antibiotic in the same container. The resultant solution is clear and transparent without turbidity or precipitate, and the efficacy of the β-lactam antibiotic and the aminoglycoside antibiotic is maintained for at least 8 hours.

In a class of any embodiment of this invention, a β-lactamase inhibitor is further added to the pharmaceutical composition, the resultant solution is clear and transparent without turbidity or precipitate, and the efficacy of the β-lactam antibiotic and the β-lactamase inhibitor in the composition is maintained for at least 8 hours.

In a class of any embodiment of this invention, a β-lactamase inhibitor and an aminoglycoside antibiotic are simultaneous added to the pharmaceutical composition, the resultant solution is clear and transparent without turbidity or precipitate, and the efficacy of the β-lactam antibiotic, β-lactamase inhibitor, and aminoglycoside antibiotic in the composition is maintained for at least 8 hours.

In a class of any embodiment of this invention, the β-lactam antibiotic is without limitation cefalothine, cefaloridine, cefazolin, cefapirin, cefaloglycin, cefalexin, cefadroxil, cefaclor, cefamandole, cefsulodine, cefoperazone, cefuroxime, cefotaxime, ceftizoxime, cefinenoxime, ceftriaxone, cefuzonam, cefixime, ceftazidime, ceftibuten, cefodizime, cephalosporin, cefpirome, cefepime, cefclidin, cefoxitin, cefinetazol, cefbuperazone, cefotetan, latamoxef, flomoxef, loracarbef, cefaloridine, latamoxef, cefminox, cefpiramide, cefonicid, ceforanide, cefacetrile, cefathiamidine, pheneticillin, propicillin, azidocillin, trityl penicillin, methicillin, nafcillin, oxacillin, cloxacillin, dicloxacillin, flucloxacillin, mecillinam, adicillin, ampicillin, amoxicillin, ticarcillin, carbenicillin, sulbenicillin, hetacillin, apalcillin, mezlocillin, temocillin, formidacillin, aspoxicillin, lenampicillin, azlocillin, pivampicillin, furbenicillin, phenoxymethypenicillin, metampicillin, or a pharmaceutically acceptable salt or a hydrate thereof, except for piperacillin. Particularly, the β-lactam antibiotic is cefoperazone, ceftriaxone, cefodizime, mezlocillin, or azlocillin.

In a class of any embodiment of this invention, the aminoglycoside antibiotic is without limitation streptomycin, dibekacin, kanamycin, tobramycin, amikacin, arbekacin, gentamicin, sagamicin, isopamicin, sisomicin, netilmicin, neomycin, paromoycin, etimicin, astromicin, ribostamycin, micronomicin, spectinomycin, or a pharmaceutically acceptable salt or hydrate thereof. Particularly, the aminoglycoside antibiotic is amikacin, gentamicin, or etimicin.

In a class of any embodiment of this invention, the β-lactamase inhibitor is without limitation clavulanic acid, sulbactam, sulbactam sodium, tazobactam, pharmaceutically acceptable salt or hydrate thereof. Particularly, the β-lactamase inhibitor is clavulanic acid, sulbactam, or tazobactam.

In a class of any embodiment of this invention, the buffer system is without limitation citric acid/citrate or other organic polyacid buffer system, phosphoric acid/phosphate or other inorganic acid system, acetic acid/acetate system or other organic monoacid system, arginine system and another amino acid system, tris/HCl system, or any other pharmaceutically acceptable buffer system. Particularly, the buffer system is citric acid/citrate system, phosphoric acid/phosphate system, acetic acid/acetate system, arginine system, carbonic acid/carbonate system. More particularly, the buffer system is citric acid/citrate system, phosphoric acid/phosphate system, or acetic acid/acetate system. The buffer component in the examples of this invention is sodium citrate.

In a class of any embodiment of this invention, the effective pH range of the buffer solution is between 4 and 8. Particularly, the effective pH range of the buffer solution is between 5.5 and 7.5. More particularly, the effective pH range of the buffer solution is between 6.0 and 6.75.

In a class of any embodiment of this invention, a concentration range of the buffer solution is between 1 and 500 mM; particularly, between 5 and 100 mM; and more particularly between 10 and 60 mM.

In embodiments of this invention, the ion-chelating agent, which inhibits aggregate particle formation, is ethylenediamine tetraacetic acid (EDTA), diethylenetriaminepentaacetic acid (DTPA), hydroxyethylethylenediaminetriacetic acid (HEDTA), or a pharmaceutically acceptable salt thereof; particularly, the ion-chelating agent is EDTA, HEDTA, or a sodium salt thereof; and more particularly, the ion-chelating agent is EDTA disodium salt.

The pharmaceutical compositions described herein can be divided in four classes according to their clinical applications, as follows:

1) In the first class is a pharmaceutical composition, comprising: at least one β-lactam antibiotic, at least one β-lactamase inhibitor, at least one aminoglycoside antibiotic, a buffer solution, and an ion-chelating agent. This pharmaceutical composition, formulated as an injectable solution, is clear and transparent without turbidity or precipitate, and the efficacy of the β-lactam antibiotic and the aminoglycoside antibiotic in this composition is maintained for a prolonged period of time. A representative unit-dose composition in this class, comprises: between 0.1 g and 5 g of β-lactam antibiotic, between 0.1 g and 5 g of β-lactamase inhibitor, between 0.1 mg and 100 mg of EDTA, between 0.01 g and 5 g of sodium citrate, and between 0.01 g and 5 g of an aminoglycoside antibiotic. The pharmaceutical composition can be prepared as a solution preparation with freeze preservation, or as an injectable powder, or a lyophilized injectable powder, which is dissolved prior to use.

2) In the second class is a pharmaceutical composition, comprising: at least one β-lactam antibiotic, at least one β-lactamase inhibitor, at least one aminoglycoside antibiotic, and an ion-chelating agent. A buffer component is required to adjust the pH value to between 6 and 7 when the composition is prepared as a solution (a suitable buffer component is citric acid/citrate). This pharmaceutical composition, formulated as an injectable solution, is clear and transparent without turbidity or precipitate, and the efficacy of the β-lactam antibiotic and the aminoglycoside antibiotic in this composition is maintained for a prolonged period of time. A representative unit-dose composition in this class, comprises: between 0.1 g and 5 g of β-lactam antibiotic, between 0.1 g and 5 g of a β-lactamase inhibitor, between 0.1 mg and 100 mg of EDTA, and between 0.01 g and 5 g of an aminoglycoside antibiotic. The pharmaceutical composition can be prepared as a solution preparation stored with freeze preservation, or as an injectable powder, or a lyophilized injectable powder, which is dissolved prior to use.

3) In the third class is a pharmaceutical composition, comprising: at least one β-lactam antibiotic, at least one β-lactamase inhibitor, and an ion-chelating agent. When the pharmaceutical composition, formulated as an injectable solution, is mixed in a container with at least a solution of an aminoglycoside antibiotic, a buffer component is required in order to obtain a clear and transparent mixture without turbidity or precipitate. The buffer component is particularly citric acid/citrate to adjust the pH value to between 6 and 7. The efficacy of the β-lactam antibiotic and the aminoglycoside antibiotic is maintained for a prolonged period of time. A representative unit-dose composition in this class, comprises: between 0.1 g and 5 g of a β-lactam antibiotic, between 0.1 g and 5 g of a β-lactamase inhibitor, and between 0.1 mg and 100 mg of EDTA. The pharmaceutical composition can be prepared as a solution preparation stored with freeze preservation, or as an injectable powder, or a lyophilized injectable powder, which is dissolved prior to use.

4) In the fourth class is a pharmaceutical composition, comprising: at least one β-lactam antibiotic, at least one β-lactamase inhibitor, a buffer solution, and an ion-chelating agent. When the pharmaceutical composition, formulated as an injectable solution, is mixed in a container with at least a solution of an aminoglycoside antibiotic, a clear and transparent mixture without turbidity or precipitate is obtained. The efficacy of the β-lactam antibiotic and the aminoglycoside antibiotic is maintained for a prolonged period of time. A representative unit-dose composition in this class, comprises: between 0.1 g and 5 g of a β-lactam antibiotic, between 0.1 g and 5 g of a β-lactamase inhibitor, between 0.01 g and 5 g of sodium citrate, and between 0.1 mg and 100 mg of EDTA. The pharmaceutical composition can be prepared as a solution preparation stored with freeze preservation, or as an injectable powder, or a lyophilized injectable powder, which is dissolved prior to use.

For highly enzyme-resistant β-lactam antibiotic, the above-mentioned four classes of composition may not need to comprise a β-lactamase inhibitor.

Embodiments of this invention provide the following additional four classes of pharmaceutical compositions based on a specific use for the type of β-lactam antibiotic, as follows:

1) A pharmaceutical composition, comprising: at least one β-lactam antibiotic, at least one aminoglycoside antibiotic, and a buffer solution with an ion-chelating agent. A solution prepared by dissolving this composition is clear and transparent without turbidity or precipitate. The efficacy of the β-lactam antibiotic and the aminoglycoside antibiotic in the composition is maintained for a prolonged period of time. A representative unit-dose composition in this class, comprises: between 0.1 g and 5 g of a β-lactam antibiotic, between 0.1 mg and 100 mg of EDTA, between 0.01 g and 5 g of sodium citrate, and between 0.01 g and 5 g of an aminoglycoside antibiotic. The pharmaceutical composition can be prepared as a solution preparation stored with freeze preservation, or as an injectable powder, or a lyophilized injectable powder, which is dissolved prior to use.

2) A pharmaceutical composition, comprising: at least one β-lactam antibiotic, at least one aminoglycoside antibiotic, and an ion-chelating agent. A buffer component is required to adjust the pH value to between 6 and 7. A particular buffer component is citric acid/citrate. A solution prepared by dissolving this composition is clear and transparent without turbidity or precipitate. The efficacy of the β-lactam antibiotic and the aminoglycoside antibiotic in the composition is maintained for a prolonged period of time. A representative unit-dose composition in this class, comprises: between 0.1 g and 5 g of a β-lactam antibiotic, between 0.1 mg and 100 mg of EDTA, and between 0.01 g and 5 g of an aminoglycoside antibiotic. The pharmaceutical composition can be prepared as a solution preparation stored with freeze preservation, or as an injectable powder, or a lyophilized injectable powder, which is dissolved prior to use.

3) A pharmaceutical composition, comprising: at least one β-lactam antibiotic, and an ion-chelating agent. When the pharmaceutical composition, formulated as an injectable solution, is mixed in a container with at least a solution of an aminoglycoside antibiotic, a buffer component is required in order to obtain a clear and transparent mixture without turbidity or precipitate. The buffer component is particularly citric acid/citrate to adjust the pH value to between 6 and 7. The efficacy of the β-lactam antibiotic and the aminoglycoside antibiotic in the composition is maintained for a prolonged period of time. A representative unit-dose composition in this class, comprises: between 0.1 g and 5 g of a β-lactam antibiotic, and between 0.1 mg and 100 mg of EDTA. The pharmaceutical composition can be prepared as a solution preparation stored with freeze preservation, or as an injectable powder, or a lyophilized injectable powder, which is dissolved prior to use.

4) A pharmaceutical composition, comprising: at least one β-lactam antibiotic, a buffer solution, and an ion-chelating agent. When the pharmaceutical composition, formulated as an injectable solution, is mixed in a container with at least a solution of an aminoglycoside antibiotic, a clear and transparent mixture without turbidity or precipitate is obtained. The efficacy of the β-lactam antibiotic and the aminoglycoside antibiotic in the composition is maintained for a prolonged period of time. A representative unit-dose composition in this class, comprises: between 0.1 g and 5 g of a β-lactam antibiotic, between 0.01 g and 5 g of sodium citrate, and between 0.1 mg and 100 mg of EDTA. The pharmaceutical composition can be prepared as a solution preparation stored with freeze preservation, or as an injectable powder, or a lyophilized injectable powder, which is dissolved prior to use.

In clinical application of the pharmaceutical composition of the invention, salts or hydrates of β-lactam antibiotics are preferable.

In clinical application of the pharmaceutical composition of the invention, if a β-lactamase inhibitor is needed, the salt of β-lactamase inhibitor such as sodium clavulanate, sulbactam sodium, or tazobactam sodium, or a hydrate thereof is preferable.

In clinical application of the pharmaceutical composition of the invention, the weight ratio of β-lactam antibiotic to β-lactamase inhibitor can be preferably 1:1, 2:1, 4:1 or 8:1.

The pharmaceutical compositions described herein include, but are not limited, to the following representative unit dose formulations:

Formulation 1: cefoperazone sodium 0.1-4 g, sulbactam sodium 0.1-4 g, disodium EDTA 0.1-100 mg, amikacin sulfate 20-800 mg, sodium citrate 10-5000 mg, and citric acid 20-5000 mg.

Formulation 2: cefoperazone sodium 0.5-4 g, sulbactam sodium 0.1-4 g, disodium EDTA 0.1-100 mg, gentamicin 20-800 mg, sodium citrate 10-5000 mg, and citric acid 20-1200 mg.

Formulation 3: cefoperazone sodium 0.5-4 g, sulbactam sodium 0.1-4 g, disodium EDTA 0.1-100 mg, tobramycin 20-800 mg, sodium citrate 10-5000 mg, and citric acid 20-1200 mg.

Formulation 4: cefoperazone sodium 0.5-4 g, sulbactam sodium 0.1-4 g, disodium EDTA 0.1-100 mg, etimicin 20-800 mg, sodium citrate 10-5000 mg, and citric acid 20-1200 mg.

Formulation 5: cefoperazone sodium 0.5-4 g, sulbactam sodium 0.1-4 g, disodium EDTA 0.1-100 mg, dibekacin 20-800 mg, sodium citrate 10-5000 mg, and citric acid 20-1200 mg.

Formulation 6: cefoperazone sodium 0.5-4 g, sulbactam sodium 0.1-4 g, disodium EDTA 0.1-100 mg, arbekacin 20-800 mg, sodium citrate 10-5000 mg, and citric acid 20-1200 mg.

Formulation 7: cefoperazone sodium 0.5-4 g, sulbactam sodium 0.1-4 g, disodium EDTA 0.1-100 mg, kanamycin 20-800 mg, sodium citrate 10-5000 mg, and citric acid 20-1200 mg.

Formulation 8: cefoperazone sodium 0.5-4 g, sulbactam sodium 0.1-4 g, disodium EDTA 0.1-100 mg, sagamicin 20-800 mg, sodium citrate 10-5000 mg, and citric acid 20-1200 mg.

Formulation 9: cefoperazone sodium 0.5-4 g, sulbactam sodium 0.1-4 g, disodium EDTA 0.1-100 mg, isopamicin 20-800 mg, sodium citrate 10-5000 mg, and citric acid 20-1200 mg.

Formulation 10: cefoperazone sodium 0.5-4 g, sulbactam sodium 0.1-4 g, disodium EDTA 0.1-100 mg, neomycin 20-800 mg, sodium citrate 10-5000 mg, and citric acid 20-1200 mg.

Formulation 11: cefoperazone sodium 0.5-4 g, sulbactam sodium 0.1-4 g, disodium EDTA 0.1-100 mg, paromoycin 20-800 mg, sodium citrate 10-5000 mg, and citric acid 20-1200 mg.

Formulation 12: cefoperazone sodium 0.5-4 g, sulbactam sodium 0.1-4 g, disodium EDTA 0.1-100 mg, sisomicin 20-800 mg, sodium citrate 10-5000 mg, and citric acid 20-1200 mg.

Formulation 13: cefoperazone sodium 0.5-4 g, sulbactam sodium 0.1-4 g, disodium EDTA 0.1-100 mg, netilmicin 20-800 mg, sodium citrate 10-5000 mg, and citric acid 20-1200 mg.

Formulation 14: cefoperazone sodium 0.5-4 g, tazobactam 0.1-4 g, disodium EDTA 0.1-100 mg, netilmicin 20-800 mg, sodium citrate 10-5000 mg, and citric acid 20-1200 mg.

Formulation 15: cefoperazone sodium 0.5-4 g, tazobactam 0.1-4 g, disodium EDTA 0.1-100 mg, amikacin sulfate 20-800 mg, sodium citrate 10-5000 mg, and citric acid 20-1200 mg.

Formulation 16: cefoperazone sodium 0.5-4 g, tazobactam 0.1-4 g, disodium EDTA 0.1-100 mg, gentamicin 20-800 mg, sodium citrate 10-5000 mg, and citric acid 20-1200 mg.

Formulation 17: cefoperazone sodium 0.5-4 g, tazobactam 0.1-4 g, disodium EDTA 0.1-100 mg, tobramycin 20-800 mg, sodium citrate 10-5000 mg, and citric acid 20-1200 mg.

Formulation 18: cefoperazone sodium 0.5-4 g, tazobactam 0.1-4 g, disodium EDTA 0.1-100 mg, etimicin 20-800 mg, sodium citrate 10-5000 mg, and citric acid 20-1200 mg.

Formulation 19: cefoperazone sodium 0.5-4 g, tazobactam 0.1-4 g, disodium EDTA 0.1-100 mg, dibekacin 20-800 mg, sodium citrate 10-5000 mg, and citric acid 20-1200 mg.

Formulation 20: cefoperazone sodium 0.5-4 g, tazobactam 0.1-4 g, disodium EDTA 0.1-100 mg, arbekacin 20-800 mg, sodium citrate 10-5000 mg, and citric acid 20-1200 mg.

Formulation 21: cefoperazone sodium 0.5-4 g, tazobactam 0.1-4 g, disodium EDTA 0.1-100 mg, kanamycin 20-800 mg, sodium citrate 10-5000 mg, and citric acid 20-1200 mg.

Formulation 22: cefoperazone sodium 0.5-4 g, tazobactam 0.1-4 g, disodium EDTA 0.1-100 mg, sagamicin 20-800 mg, sodium citrate 10-5000 mg, and citric acid 20-1200 mg.

Formulation 23: cefoperazone sodium 0.5-4 g, tazobactam 0.1-4 g, disodium EDTA 0.1-100 mg, isopamicin 20-800 mg, sodium citrate 10-5000 mg, and citric acid 20-1200 mg.

Formulation 24: cefoperazone sodium 0.5-4 g, tazobactam 0.1-4 g, disodium EDTA 0.1-100 mg, neomycin 20-800 mg, sodium citrate 10-5000 mg, and citric acid 20-1200 mg.

Formulation 25: cefoperazone sodium 0.5-4 g, tazobactam 0.1-4 g, disodium EDTA 0.1-100 mg, paromoycin 20-800 mg, sodium citrate 10-5000 mg, and citric acid 20-1200 mg.

Formulation 26: cefoperazone sodium 0.5-4 g, tazobactam 0.1-4 g, disodium EDTA 0.1-100 mg, sisomicin 20-800 mg, sodium citrate 10-5000 mg, and citric acid 20-1200 mg.

Formulation 27: cefodizime sodium 0.5-4 g, disodium EDTA 0.1-100 mg, netilmicin 20-800 mg, sodium citrate 10-5000 mg, and citric acid 20-1200 mg.

Formulation 28: cefodizime sodium 0.5-4 g, disodium EDTA 0.1-100 mg, amikacin sulfate 20-800 mg, sodium citrate 10-5000 mg, and citric acid 20-1200 mg.

Formulation 29: cefodizime sodium 0.5-4 g, disodium EDTA 0.1-100 mg, gentamicin 20-800 mg, sodium citrate 10-5000 mg, and citric acid 20-1200 mg.

Formulation 30: cefodizime sodium 0.5-4 g, disodium EDTA 0.1-100 mg, tobramycin 20-800 mg, sodium citrate 10-5000 mg, and citric acid 20-1200 mg.

Formulation 31: cefodizime sodium 0.5-4 g, disodium EDTA 0.1-100 mg, etimicin 20-800 mg, sodium citrate 10-5000 mg, and citric acid 20-1200 mg.

Formulation 32: cefodizime sodium 0.5-4 g, disodium EDTA 0.1-100 mg, dibekacin 20-800 mg, sodium citrate 10-5000 mg, and citric acid 20-1200 mg.

Formulation 33: cefodizime sodium 0.5-4 g, disodium EDTA 0.1-100 mg, arbekacin 20-800 mg, sodium citrate 10-5000 mg, and citric acid 20-1200 mg.

Formulation 34: cefodizime sodium 0.5-4 g, disodium EDTA 0.1-100 mg, kanamycin 20-800 mg, sodium citrate 10-5000 mg, and citric acid 20-1200 mg.

Formulation 35: cefodizime sodium 0.5-4 g, disodium EDTA 0.1-100 mg, sagamicin 20-800 mg, sodium citrate 10-5000 mg, and citric acid 20-1200 mg.

Formulation 36: cefodizime sodium 0.5-4 g, disodium EDTA 0.1-100 mg, isopamicin 20-800 mg, sodium citrate 10-5000 mg, and citric acid 20-1200 mg.

Formulation 37: cefodizime sodium 0.5-4 g, disodium EDTA 0.1-100 mg, neomycin 20-800 mg, sodium citrate 10-5000 mg, and citric acid 20-1200 mg.

Formulation 38: cefodizime sodium 0.5-4 g, disodium EDTA 0.1-100 mg, paromoycin 20-800 mg, sodium citrate 10-5000 mg, and citric acid 20-1200 mg.

Formulation 39: cefodizime sodium 0.5-4 g, disodium EDTA 0.1-100 mg, sisomicin 20-800 mg, sodium citrate 10-5000 mg, and citric acid 20-1200 mg.

Formulation 40: cefoperazone sodium 0.5-4 g, potassium clavulanate 0.1-4 g, netilmicin 20-800 mg, disodium EDTA 0.1-100 mg, sodium citrate 10-5000 mg, and citric acid 20-1200 mg.

Formulation 41: cefoperazone sodium 0.5-4 g, potassium clavulanate 0.1-4 g, amikacin sulfate 20-800 mg, disodium EDTA 0.1-100 mg, sodium citrate 10-5000 mg, and citric acid 20-1200 mg.

Formulation 42: cefoperazone sodium 0.5-4 g, potassium clavulanate 0.1-4 g, gentamicin 20-800 mg, disodium EDTA 0.1-100 mg, sodium citrate 10-5000 mg, and citric acid 20-1200 mg.

Formulation 43: cefoperazone sodium 0.5-4 g, potassium clavulanate 0.1-4 g, tobramycin 20-800 mg, disodium EDTA 0.1-100 mg, sodium citrate 10-5000 mg, and citric acid 20-1200 mg.

Formulation 44: cefoperazone sodium 0.5-4 g, potassium clavulanate 0.1-4 g, etimicin 20-800 mg, disodium EDTA 0.1-100 mg, sodium citrate 10-5000 mg, and citric acid 20-1200 mg.

Formulation 45: cefoperazone sodium 0.5-4 g, potassium clavulanate 0.1-4 g, dibekacin 20-800 mg, disodium EDTA 0.1-100 mg, sodium citrate 10-5000 mg, and citric acid 20-1200 mg.

Formulation 46: cefoperazone sodium 0.5-4 g, potassium clavulanate 0.1-4 g, arbekacin 20-800 mg, disodium EDTA 0.1-100 mg, sodium citrate 10-5000 mg, and citric acid 20-1200 mg.

Formulation 47: cefoperazone sodium 0.5-4 g, potassium clavulanate 0.1-4 g, kanamycin 20-800 mg, disodium EDTA 0.1-100 mg, sodium citrate 10-5000 mg, and citric acid 20-1200 mg.

Formulation 48: cefoperazone sodium 0.5-4 g, potassium clavulanate 0.1-4 g, sagamicin 20-800 mg, disodium EDTA 0.1-100 mg, sodium citrate 10-5000 mg, and citric acid 20-1200 mg.

Formulation 49: cefoperazone sodium 0.5-4 g, potassium clavulanate 0.1-4 g, isopamicin 20-800 mg, disodium EDTA 0.1-100 mg, sodium citrate 10-5000 mg, and citric acid 20-1200 mg.

Formulation 50: cefoperazone sodium 0.5-4 g, potassium clavulanate 0.1-4 g, neomycin 20-800 mg, disodium EDTA 0.1-100 mg, sodium citrate 10-5000 mg, and citric acid 20-1200 mg.

Formulation 51: cefoperazone sodium 0.5-4 g, potassium clavulanate 0.1-4 g, paromoycin 20-800 mg, disodium EDTA 0.1-100 mg, sodium citrate 10-5000 mg, and citric acid 20-1200 mg.

Formulation 52: cefoperazone sodium 0.5-4 g, potassium clavulanate 0.1-4 g, sisomicin 20-800 mg, disodium EDTA 0.1-100 mg, sodium citrate 10-5000 mg, and citric acid 20-1200 mg.

Formulation 53: ceftriaxone sodium 0.5-4 g, netilmicin 20-800 mg, disodium EDTA 0.1-100 mg, sodium citrate 10-5000 mg, and citric acid 20-1200 mg.

Formulation 54: ceftriaxone sodium 0.5-4 g, amikacin sulfate 20-800 mg, disodium EDTA 0.1-100 mg, sodium citrate 10-5000 mg, and citric acid 20-1200 mg.

Formulation 55: ceftriaxone sodium 0.5-4 g, gentamicin 20-800 mg, disodium EDTA 0.1-100 mg, sodium citrate 10-5000 mg, and citric acid 20-1200 mg.

Formulation 56: ceftriaxone sodium 0.5-4 g, tobramycin 20-800 mg, disodium EDTA 0.1-100 mg, sodium citrate 10-5000 mg, and citric acid 20-1200 mg.

Formulation 57: ceftriaxone sodium 0.5-4 g, etimicin 20-800 mg, disodium EDTA 0.1-100 mg, sodium citrate 10-5000 mg, and citric acid 20-1200 mg.

Formulation 58: ceftriaxone sodium 0.5-4 g, dibekacin 20-800 mg, disodium EDTA 0.1-100 mg, sodium citrate 10-5000 mg, and citric acid 20-1200 mg.

Formulation 59: ceftriaxone sodium 0.5-4 g, arbekacin 20-800 mg, disodium EDTA 0.1-100 mg, sodium citrate 10-5000 mg, and citric acid 20-1200 mg.

Formulation 60: ceftriaxone sodium 0.5-4 g, kanamycin 20-800 mg, disodium EDTA 0.1-100 mg, sodium citrate 10-5000 mg, and citric acid 20-1200 mg.

Formulation 61: ceftriaxone sodium 0.5-4 g, sagamicin 20-800 mg, disodium EDTA 0.1-100 mg, sodium citrate 10-5000 mg, and citric acid 20-1200 mg.

Formulation 62: ceftriaxone sodium 0.5-4 g, isopamicin 20-800 mg, disodium EDTA 0.1-100 mg, sodium citrate 10-5000 mg, and citric acid 20-1200 mg.

Formulation 63: ceftriaxone sodium 0.5-4 g, neomycin 20-800 mg, disodium EDTA 0.1-100 mg, sodium citrate 10-5000 mg, and citric acid 20-1200 mg.

Formulation 64: ceftriaxone sodium 0.5-4 g, paromoycin 20-800 mg, disodium EDTA 0.1-100 mg, sodium citrate 10-5000 mg, and citric acid 20-1200 mg.

Formulation 65: ceftriaxone sodium 0.5-4 g, sisomicin 20-800 mg, disodium EDTA 0.1-100 mg, sodium citrate 10-5000 mg, and citric acid 20-1200 mg.

Formulation 66: ceftriaxone sodium 0.5-4 g, sulbactam sodium 0.1-4 g, netilmicin 20-800 mg, disodium EDTA 0.1-100 mg, sodium citrate 10-5000 mg, and citric acid 20-1200 mg.

Formulation 67: ceftriaxone sodium 0.5-4 g, sulbactam sodium 0.1-4 g, amikacin sulfate 20-800 mg, disodium EDTA 0.1-100 mg, sodium citrate 10-5000 mg, and citric acid 20-1200 mg.

Formulation 68: ceftriaxone sodium 0.5-4 g, sulbactam sodium 0.1-4 g, gentamicin 20-800 mg, disodium EDTA 0.1-100 mg, sodium citrate 10-5000 mg, and citric acid 20-1200 mg.

Formulation 69: ceftriaxone sodium 0.5-4 g, sulbactam sodium 0.1-4 g, tobramycin 20-800 mg, disodium EDTA 0.1-100 mg, sodium citrate 10-5000 mg, and citric acid 20-1200 mg.

Formulation 70: ceftriaxone sodium 0.5-4 g, sulbactam sodium 0.1-4 g, etimicin 20-800 mg, disodium EDTA 0.1-100 mg, sodium citrate 10-5000 mg, and citric acid 20-1200 mg.

Formulation 71: ceftriaxone sodium 0.5-4 g, sulbactam sodium 0.1-4 g, dibekacin 20-800 mg, disodium EDTA 0.1-100 mg, sodium citrate 10-5000 mg, and citric acid 20-1200 mg.

Formulation 72: ceftriaxone sodium 0.5-4 g, sulbactam sodium 0.1-4 g, arbekacin 20-800 mg, disodium EDTA 0.1-100 mg, sodium citrate 10-5000 mg, and citric acid 20-1200 mg.

Formulation 73: ceftriaxone sodium 0.5-4 g, sulbactam sodium 0.1-4 g, kanamycin 20-800 mg, disodium EDTA 0.1-100 mg, sodium citrate 10-5000 mg, and citric acid 20-1200 mg.

Formulation 74: ceftriaxone sodium 0.5-4 g, sulbactam sodium 0.1-4 g, sagamicin 20-800 mg, disodium EDTA 0.1-100 mg, sodium citrate 10-5000 mg, and citric acid 20-1200 mg.

Formulation 75: ceftriaxone sodium 0.5-4 g, sulbactam sodium 0.1-4 g, isopamicin 20-800 mg, disodium EDTA 0.1-100 mg, sodium citrate 10-5000 mg, and citric acid 20-1200 mg.

Formulation 76: ceftriaxone sodium 0.5-4 g, sulbactam sodium 0.1-4 g, neomycin 20-800 mg, disodium EDTA 0.1-100 mg, sodium citrate 10-5000 mg, and citric acid 20-1200 mg.

Formulation 77: ceftriaxone sodium 0.5-4 g, sulbactam sodium 0.1-4 g, paromoycin 20-800 mg, disodium EDTA 0.1-100 mg, sodium citrate 10-5000 mg, and citric acid 20-1200 mg.

Formulation 78: ceftriaxone sodium 0.5-4 g, sulbactam sodium 0.1-4 g, sisomicin 20-800 mg, disodium EDTA 0.1-100 mg, sodium citrate 10-5000 mg, and citric acid 20-1200 mg.

Formulation 79: cefoperazone sodium 0.5-4 g, potassium clavulanate 0.1-5 g, disodium EDTA 0.1-100 mg, sodium citrate 10-5000 mg, and citric acid 20-1200 mg.

Formulation 80: cefsulodine sodium 0.5-4 g, potassium clavulanate 0.1-5 g, disodium EDTA 0.1-100 mg, sodium citrate 10-5000 mg, and citric acid 20-1200 mg.

Formulation 81: cefamandole sodium 0.5-4 g, potassium clavulanate 0.1-5 g, disodium EDTA 0.1-100 mg, sodium citrate 10-5000 mg, and citric acid 20-1200 mg.

Formulation 82: cefadroxil sodium 0.5-4 g, potassium clavulanate 0.1-5 g, disodium EDTA 0.1-100 mg, sodium citrate 10-5000 mg, and citric acid 20-1200 mg.

Formulation 83: cefaclor sodium 0.5-4 g, potassium clavulanate 0.1-5 g, disodium EDTA 0.1-100 mg, sodium citrate 10-5000 mg, and citric acid 20-1200 mg.

Formulation 84: cefalexin sodium 0.5-4 g, potassium clavulanate 0.1-5 g, disodium EDTA 0.1-100 mg, sodium citrate 10-5000 mg, and citric acid 20-1200 mg.

Formulation 85: cefaloglycin sodium 0.5-4 g, potassium clavulanate 0.1-5 g, disodium EDTA 0.1-100 mg, sodium citrate 10-5000 mg, and citric acid 20-1200 mg.

Formulation 86: cephapirin sodium 0.5-4 g, potassium clavulanate 0.1-5 g, disodium EDTA 0.1-100 mg, sodium citrate 10-5000 mg, and citric acid 20-1200 mg.

Formulation 87: cefazolin sodium 0.5-4 g, potassium clavulanate 0.1-5 g, disodium EDTA 0.1-100 mg, sodium citrate 10-5000 mg, and citric acid 20-1200 mg.

Formulation 88: cefalothine sodium 0.5-4 g, potassium clavulanate 0.1-5 g, disodium EDTA 0.1-100 mg, sodium citrate 10-5000 mg, and citric acid 20-1200 mg.

Formulation 89: cefoperazone 0.5-4 g, sulbactam 0.1-4 g, arginine 100-2000 mg, and disodium EDTA 0.1-100 mg.

Formulation 90: cefoperazone 0.5-4 g, sulbactam 0.1-4 g, arginine 100-2000 mg, disodium EDTA 0.1-100 mg, and gentamicin 20-800 mg.

Formulation 91: cefoperazone 0.5-4 g, arginine 100-5000 mg, and disodium EDTA 0.1-100 mg.

Formulation 92: cefbuperazone sodium 0.5-4 g, disodium EDTA 0.1-100 mg, sodium citrate 10-5000 mg, and citric acid 20-1200 mg.

Formulation 93: cefotetan sodium 0.5-4 g, disodium EDTA 0.1-100 mg, sodium citrate 10-5000 mg, and citric acid 20-1200 mg.

Formulation 94: latamoxef sodium 0.5-4 g, disodium EDTA 0.1-100 mg, sodium citrate 10-5000 mg, and citric acid 20-1200 mg.

Formulation 95: flomoxef sodium 0.5-4 g, disodium EDTA 0.1-100 mg, sodium citrate 10-5000 mg, and citric acid 20-1200 mg.

Formulation 96: loracarbef sodium 0.5-4 g, disodium EDTA 0.1-100 mg, sodium citrate 10-5000 mg, and citric acid 20-1200 mg.

Formulation 97: cefmetazol sodium 0.5-4 g, disodium EDTA 0.1-100 mg, sodium citrate 10-5000 mg, and citric acid 20-1200 mg.

Formulation 98: cefoxitin sodium 0.5-4 g, disodium EDTA 0.1-100 mg, sodium citrate 10-5000 mg, and citric acid 20-1200 mg.

Formulation 99: cefclidin sodium 0.5-4 g, disodium EDTA 0.1-100 mg, sodium citrate 10-5000 mg, and citric acid 20-1200 mg.

Formulation 100: cefpirome sodium 0.5-4 g, disodium EDTA 0.1-100 mg, sodium citrate 10-5000 mg, and citric acid 20-1200 mg.

Formulation 101: cephalosporin sodium 0.5-4 g, disodium EDTA 0.1-100 mg, sodium citrate 10-5000 mg, and citric acid 20-1200 mg.

Formulation 102: cefodizime sodium 0.5-4 g, disodium EDTA 0.1-100 mg, sodium citrate 10-5000 mg, and citric acid 20-1200 mg.

Formulation 103: ceftibuten sodium 0.5-4 g, disodium EDTA 0.1-100 mg, sodium citrate 10-5000 mg, and citric acid 20-1200 mg.

Formulation 104: ceftazidime sodium 0.5-4 g, disodium EDTA 0.1-100 mg, sodium citrate 10-5000 mg, and citric acid 20-1200 mg.

Formulation 105: cefixime sodium 0.5-4 g, disodium EDTA 0.1-100 mg, sodium citrate 10-5000 mg, and citric acid 20-1200 mg.

Formulation 106: cefuzonam sodium 0.5-4 g, disodium EDTA 0.1-100 mg, sodium citrate 10-5000 mg, and citric acid 20-1200 mg.

Formulation 107: ceftriaxone sodium 0.5-4 g, disodium EDTA 0.1-100 mg, sodium citrate 10-5000 mg, and citric acid 20-1200 mg.

Formulation 109: cefmenoxime sodium 0.5-4 g, disodium EDTA 0.1-100 mg, sodium citrate 10-5000 mg, and citric acid 20-1200 mg.

Formulation 110: ceftizoxime sodium 0.5-4 g, disodium EDTA 0.1-100 mg, sodium citrate 10-5000 mg, and citric acid 20-1200 mg.

Formulation 111: cefotaxime sodium 0.5-4 g, disodium EDTA 0.1-100 mg, sodium citrate 10-5000 mg, and citric acid 20-1200 mg.

Formulation 112: cefuroxime sodium 0.5-4 g, disodium EDTA 0.1-100 mg, sodium citrate 10-5000 mg, and citric acid 20-1200 mg.

Formulation 113: cefoperazone sodium 0.5-4 g, disodium EDTA 0.1-100 mg, sodium citrate 10-5000 mg, and citric acid 20-1200 mg.

Formulation 114: cefsulodin sodium 0.5-4 g, disodium EDTA 0.1-100 mg, sodium citrate 10-5000 mg, and citric acid 20-1200 mg.

Formulation 115: cefamandole sodium 0.5-4 g, disodium EDTA 0.1-100 mg, sodium citrate 10-5000 mg, and citric acid 20-1200 mg.

Formulation 116: cefadroxil sodium 0.5-4 g, disodium EDTA 0.1-100 mg, sodium citrate 10-5000 mg, and citric acid 20-1200 mg.

Formulation 117: cefaclor sodium 0.5-4 g, disodium EDTA 0.1-100 mg, sodium citrate 10-5000 mg, and citric acid 20-1200 mg.

Formulation 118: cefalexin sodium 0.5-4 g, disodium EDTA 0.1-100 mg, sodium citrate 10-5000 mg, and citric acid 20-1200 mg.

Formulation 119: cefaloglycin sodium 0.5-4 g, disodium EDTA 0.1-100 mg, sodium citrate 10-5000 mg, and citric acid 20-1200 mg.

Formulation 120: cefapirin sodium 0.5-4 g, disodium EDTA 0.1-100 mg, sodium citrate 10-5000 mg, and citric acid 20-1200 mg.

Formulation 121: cefazolin sodium 0.5-4 g, disodium EDTA 0.1-100 mg, sodium citrate 10-5000 mg, and citric acid 20-1200 mg.

Formulation 122: cefalothine sodium 0.5-4 g, disodium EDTA 0.1-100 mg, sodium citrate 10-5000 mg, and citric acid 20-1200 mg.

Formulation 123: pheneticillin sodium 0.5-4 g, disodium EDTA 0.1-100 mg, sodium citrate 10-5000 mg, and citric acid 20-1200 mg.

Formulation 124: propicillin sodium 0.5-4 g, disodium EDTA 0.1-100 mg, sodium citrate 10-5000 mg, and citric acid 20-1200 mg.

Formulation 125: azidocillin sodium 0.5-4 g, disodium EDTA 0.1-100 mg, sodium citrate 10-5000 mg, and citric acid 20-1200 mg.

Formulation 126: trityl penicillin sodium 0.5-4 g, disodium EDTA 0.1-100 mg, sodium citrate 10-5000 mg, and citric acid 20-1200 mg.

Formulation 127: methicillin sodium 0.5-4 g, disodium EDTA 0.1-100 mg, sodium citrate 10-5000 mg, and citric acid 20-1200 mg.

Formulation 128: nafcillin sodium 0.5-4 g, disodium EDTA 0.1-100 mg, sodium citrate 10-5000 mg, and citric acid 20-1200 mg.

Formulation 129: oxacillin sodium 0.5-4 g, disodium EDTA 0.1-100 mg, sodium citrate 10-5000 mg, and citric acid 20-1200 mg.

Formulation 130: cloxacillin sodium 0.5-4 g, disodium EDTA 0.1-100 mg, sodium citrate 10-5000 mg, and citric acid 20-1200 mg.

Formulation 131: dicloxacillin sodium 0.5-4 g, disodium EDTA 0.1-100 mg, sodium citrate 10-5000 mg, and citric acid 20-1200 mg.

Formulation 132: flucloxacillin sodium 0.5-4 g, disodium EDTA 0.1-100 mg, sodium citrate 10-5000 mg, and citric acid 20-1200 mg.

Formulation 133: mecillinam sodium 0.5-4 g, disodium EDTA 0.1-100 mg, sodium citrate 10-5000 mg, and citric acid 20-1200 mg.

Formulation 134: adicillin sodium 0.5-4 g, disodium EDTA 0.1-100 mg, sodium citrate 10-5000 mg, and citric acid 20-1200 mg.

Formulation 135: ampicillin sodium 0.5-4 g, disodium EDTA 0.1-100 mg, sodium citrate 10-5000 mg, and citric acid 20-1200 mg.

Formulation 136: amoxicillin sodium 0.5-4 g, disodium EDTA 0.1-100 mg, sodium citrate 10-5000 mg, and citric acid 20-1200 mg.

Formulation 137: ticarcillin sodium 0.5-4 g, disodium EDTA 0.1-100 mg, sodium citrate 10-5000 mg, and citric acid 20-1200 mg.

Formulation 138: carbenicillin sodium 0.5-4 g, disodium EDTA 0.1-100 mg, sodium citrate 10-5000 mg, and citric acid 20-1200 mg.

Formulation 139: sulbenicillin sodium 0.5-4 g, disodium EDTA 0.1-100 mg, sodium citrate 10-5000 mg, and citric acid 20-1200 mg.

Formulation 140: hetacillin sodium 0.5-4 g, disodium EDTA 0.1-100 mg, sodium citrate 10-5000 mg, and citric acid 20-1200 mg.

Formulation 141: apalcillin sodium 0.5-4 g, disodium EDTA 0.1-100 mg, sodium citrate 10-5000 mg, and citric acid 20-1200 mg.

Formulation 142: mezlocillin sodium 0.5-4 g, disodium EDTA 0.1-100 mg, sodium citrate 10-5000 mg, and citric acid 20-1200 mg.

Formulation 143: temocillin sodium 0.5-4 g, disodium EDTA 0.1-100 mg, sodium citrate 10-5000 mg, and citric acid 20-1200 mg.

Formulation 144: formidacillin sodium 0.5-4 g, disodium EDTA 0.1-100 mg, sodium citrate 10-5000 mg, and citric acid 20-1200 mg.

Formulation 145: aspoxicillin sodium 0.5-4 g, disodium EDTA 0.1-100 mg, sodium citrate 10-5000 mg, and citric acid 20-1200 mg.

Formulation 146: lenampicillin sodium 0.5-4 g, disodium EDTA 0.1-100 mg, sodium citrate 10-5000 mg, and citric acid 20-1200 mg.

Formulation 147: pheneticillin sodium 0.5-4 g, sulbactam sodium 0.05-5 g, disodium EDTA 0.1-100 mg, sodium citrate 10-5000 mg, and citric acid 20-1200 mg.

Formulation 148: propicillin sodium 0.5-4 g, sulbactam sodium 0.05-5 g, disodium EDTA 0.1-100 mg, sodium citrate 10-5000 mg, and citric acid 20-1200 mg.

Formulation 149: azidocillin sodium 0.5-4 g, sulbactam sodium 0.05-5 g, disodium EDTA 0.1-100 mg, sodium citrate 10-5000 mg, and citric acid 20-1200 mg.

Formulation 150: trityl penicillin sodium 0.5-4 g, sulbactam sodium 0.05-5 g, disodium EDTA 0.1-100 mg, sodium citrate 10-5000 mg, and citric acid 20-1200 mg.

Formulation 151: methicillin sodium 0.5-4 g, sulbactam sodium 0.05-5 g, disodium EDTA 0.1-100 mg, sodium citrate 10-5000 mg, and citric acid 20-1200 mg.

Formulation 152: nafcillin sodium 0.5-4 g, sulbactam sodium 0.05-5 g, disodium EDTA 0.1-100 mg, sodium citrate 10-5000 mg, and citric acid 20-1200 mg.

Formulation 153: oxacillin sodium 0.5-4 g, sulbactam sodium 0.05-5 g, disodium EDTA 0.1-100 mg, sodium citrate 10-5000 mg, and citric acid 20-1200 mg.

Formulation 154: cloxacillin sodium 0.5-4 g, sulbactam sodium 0.05-5 g, disodium EDTA 0.1-100 mg, sodium citrate 10-5000 mg, and citric acid 20-1200 mg.

Formulation 155: dicloxacillin sodium 0.5-4 g, sulbactam sodium 0.05-5 g, disodium EDTA 0.1-100 mg, sodium citrate 10-5000 mg, and citric acid 20-1200 mg.

Formulation 156: flucloxacillin sodium 0.5-4 g, sulbactam sodium 0.05-5 g, disodium EDTA 0.1-100 mg, sodium citrate 10-5000 mg, and citric acid 20-1200 mg.

Formulation 157: mecillinam sodium 0.5-4 g, sulbactam sodium 0.05-5 g, disodium EDTA 0.1-100 mg, sodium citrate 10-5000 mg, and citric acid 20-1200 mg.

Formulation 158: adicillin sodium 0.5-4 g, sulbactam sodium 0.05-5 g, disodium EDTA 0.1-100 mg, sodium citrate 10-5000 mg, and citric acid 20-1200 mg.

Formulation 159: ampicillin sodium 0.5-4 g, sulbactam sodium 0.05-5 g, disodium EDTA 0.1-100 mg, sodium citrate 10-5000 mg, and citric acid 20-1200 mg.

Formulation 160: amoxicillin sodium 0.5-4 g, sulbactam sodium 0.05-5 g, disodium EDTA 0.1-100 mg, sodium citrate 10-5000 mg, and citric acid 20-1200 mg.

Formulation 161: ticarcillin sodium 0.5-4 g, sulbactam sodium 0.05-5 g, disodium EDTA 0.1-100 mg, sodium citrate 10-5000 mg, and citric acid 20-1200 mg.

Formulation 162: carbenicillin sodium 0.5-4 g, sulbactam sodium 0.05-5 g, disodium EDTA 0.1-100 mg, sodium citrate 10-5000 mg, and citric acid 20-1200 mg.

Formulation 163: sulbenicillin sodium 0.5-4 g, sulbactam sodium 0.05-5 g, disodium EDTA 0.1-100 mg, sodium citrate 10-5000 mg, and citric acid 20-1200 mg.

Formulation 164: hetacillin sodium 0.5-4 g, sulbactam sodium 0.05-5 g, disodium EDTA 0.1-100 mg, sodium citrate 10-5000 mg, and citric acid 20-1200 mg.

Formulation 165: apalcillin sodium 0.5-4 g, sulbactam sodium 0.05-5 g, disodium EDTA 0.1-100 mg, sodium citrate 10-5000 mg, and citric acid 20-1200 mg.

Formulation 166: mezlocillin sodium 0.5-4 g, sulbactam sodium 0.05-5 g, disodium EDTA 0.1-100 mg, sodium citrate 10-5000 mg, and citric acid 20-1200 mg.

Formulation 167: temocillin sodium 0.5-4 g, sulbactam sodium 0.05-5 g, disodium EDTA 0.1-100 mg, sodium citrate 10-5000 mg, and citric acid 20-1200 mg.

Formulation 168: formidacillin sodium 0.5-4 g, sulbactam sodium 0.05-5 g, disodium EDTA 0.1-100 mg, sodium citrate 10-5000 mg, and citric acid 20-1200 mg.

Formulation 169: aspoxicillin sodium 0.5-4 g, sulbactam sodium 0.05-5 g, disodium EDTA 0.1-100 mg, sodium citrate 10-5000 mg, and citric acid 20-1200 mg.

Formulation 170: lenampicillin sodium 0.5-4 g, sulbactam sodium 0.05-5 g, disodium EDTA 0.1-100 mg, sodium citrate 10-5000 mg, and citric acid 20-1200 mg.

Formulation 171: pheneticillin sodium 0.5-4 g, tazobactam sodium 0.05-5 g, disodium EDTA 0.1-100 mg, sodium citrate 10-5000 mg, and citric acid 20-1200 mg.

Formulation 172: propicillin sodium 0.5-4 g, tazobactam sodium 0.05-5 g, disodium EDTA 0.1-100 mg, sodium citrate 10-5000 mg, and citric acid 20-1200 mg.

Formulation 173: azidocillin sodium 0.5-4 g, tazobactam sodium 0.05-5 g, disodium EDTA 0.1-100 mg, sodium citrate 10-5000 mg, and citric acid 20-1200 mg.

Formulation 174: trityl penicillin sodium 0.5-4 g, tazobactam sodium 0.05-5 g, disodium EDTA 0.1-100 mg, sodium citrate 10-5000 mg, and citric acid 20-1200 mg.

Formulation 175: methicillin sodium 0.5-4 g, tazobactam sodium 0.05-5 g, disodium EDTA 0.1-100 mg, sodium citrate 10-5000 mg, and citric acid 20-1200 mg.

Formulation 176: nafcillin sodium 0.5-4 g, tazobactam sodium 0.05-5 g, disodium EDTA 0.1-100 mg, sodium citrate 10-5000 mg, and citric acid 20-1200 mg.

Formulation 177: oxacillin sodium 0.5-4 g, tazobactam sodium 0.05-5 g, disodium EDTA 0.1-100 mg, sodium citrate 10-5000 mg, and citric acid 20-1200 mg.

Formulation 178: cloxacillin sodium 0.5-4 g, tazobactam sodium 0.05-5 g, disodium EDTA 0.1-100 mg, sodium citrate 10-5000 mg, and citric acid 20-1200 mg.

Formulation 179: dicloxacillin sodium 0.5-4 g, tazobactam sodium 0.05-5 g, disodium EDTA 0.1-100 mg, sodium citrate 10-5000 mg, and citric acid 20-1200 mg.

Formulation 180: flucloxacillin sodium 0.5-4 g, tazobactam sodium 0.05-5 g, disodium EDTA 0.1-100 mg, sodium citrate 10-5000 mg, and citric acid 20-1200 mg.

Formulation 181: mecillinam sodium 0.5-4 g, tazobactam sodium 0.05-5 g, disodium EDTA 0.1-100 mg, sodium citrate 10-5000 mg, and citric acid 20-1200 mg.

Formulation 182: adicillin sodium 0.5-4 g, tazobactam sodium 0.05-5 g, disodium EDTA 0.1-100 mg, sodium citrate 10-5000 mg, and citric acid 20-1200 mg.

Formulation 183: ampicillin sodium 0.5-4 g, tazobactam sodium 0.05-5 g, disodium EDTA 0.1-100 mg, sodium citrate 10-5000 mg, and citric acid 20-1200 mg.

Formulation 184: amoxicillin sodium 0.5-4 g, tazobactam sodium 0.05-5 g, disodium EDTA 0.1-100 mg, sodium citrate 10-5000 mg, and citric acid 20-1200 mg.

Formulation 185: ticarcillin sodium 0.5-4 g, tazobactam sodium 0.05-5 g, disodium EDTA 0.1-100 mg, sodium citrate 10-5000 mg, and citric acid 20-1200 mg.

Formulation 186: carbenicillin sodium 0.5-4 g, tazobactam sodium 0.05-5 g, disodium EDTA 0.1-100 mg, sodium citrate 10-5000 mg, and citric acid 20-1200 mg.

Formulation 187: sulbenicillin sodium 0.5-4 g, tazobactam sodium 0.05-5 g, disodium EDTA 0.1-100 mg, sodium citrate 10-5000 mg, and citric acid 20-1200 mg.

Formulation 188: hetacillin sodium 0.5-4 g, tazobactam sodium 0.05-5 g, disodium EDTA 0.1-100 mg, sodium citrate 10-5000 mg, and citric acid 20-1200 mg.

Formulation 189: apalcillin sodium 0.5-4 g, tazobactam sodium 0.05-5 g, disodium EDTA 0.1-100 mg, sodium citrate 10-5000 mg, and citric acid 20-1200 mg.

Formulation 190: mezlocillin sodium 0.5-4 g, tazobactam sodium 0.05-5 g, disodium EDTA 0.1-100 mg, sodium citrate 10-5000 mg, and citric acid 20-1200 mg.

Formulation 191: temocillin sodium 0.5-4 g, tazobactam sodium 0.05-5 g, disodium EDTA 0.1-100 mg, sodium citrate 10-5000 mg, and citric acid 20-1200 mg.

Formulation 192: formidacillin sodium 0.5-4 g, tazobactam sodium 0.05-5 g, disodium EDTA 0.1-100 mg, sodium citrate 10-5000 mg, and citric acid 20-1200 mg.

Formulation 193: aspoxicillin sodium 0.5-4 g, tazobactam sodium 0.05-5 g, disodium EDTA 0.1-100 mg, sodium citrate 10-5000 mg, and citric acid 20-1200 mg.

Formulation 194: lenampicillin sodium 0.5-4 g, tazobactam sodium 0.05-5 g, disodium EDTA 0.1-100 mg, sodium citrate 10-5000 mg, and citric acid 20-1200 mg.

Formulation 195: pheneticillin sodium 0.5-4 g, potassium clavulanate 0.05-5 g, disodium EDTA 0.1-100 mg, sodium citrate 10-5000 mg, and citric acid 20-1200 mg.

Formulation 196: propicillin sodium 0.5-4 g, potassium clavulanate 0.05-5 g, disodium EDTA 0.1-100 mg, sodium citrate 10-5000 mg, and citric acid 20-1200 mg.

Formulation 197: azidocillin sodium 0.5-4 g, potassium clavulanate 0.05-5 g, disodium EDTA 0.1-100 mg, sodium citrate 10-5000 mg, and citric acid 20-1200 mg.

Formulation 198: trityl penicillin sodium 0.5-4 g, potassium clavulanate 0.05-5 g, disodium EDTA 0.1-100 mg, sodium citrate 10-5000 mg, and citric acid 20-1200 mg.

Formulation 199: methicillin sodium 0.5-4 g, potassium clavulanate 0.05-5 g, disodium EDTA 0.1-100 mg, sodium citrate 10-5000 mg, and citric acid 20-1200 mg.

Formulation 200: nafcillin sodium 0.5-4 g, potassium clavulanate 0.05-5 g, disodium EDTA 0.1-100 mg, sodium citrate 10-5000 mg, and citric acid 20-1200 mg.

Formulation 201: oxacillin sodium 0.5-4 g, potassium clavulanate 0.05-5 g, disodium EDTA 0.1-100 mg, sodium citrate 10-5000 mg, and citric acid 20-1200 mg.

Formulation 202: cloxacillin sodium 0.5-4 g, potassium clavulanate 0.05-5 g, disodium EDTA 0.1-100 mg, sodium citrate 10-5000 mg, and citric acid 20-1200 mg.

Formulation 203: dicloxacillin sodium 0.5-4 g, potassium clavulanate 0.05-5 g, disodium EDTA 0.1-100 mg, sodium citrate 10-5000 mg, and citric acid 20-1200 mg.

Formulation 204: flucloxacillin sodium 0.5-4 g, potassium clavulanate 0.05-5 g, disodium EDTA 0.1-100 mg, sodium citrate 10-5000 mg, and citric acid 20-1200 mg.

Formulation 205: mecillinam sodium 0.5-4 g, potassium clavulanate 0.05-5 g, disodium EDTA 0.1-100 mg, sodium citrate 10-5000 mg, and citric acid 20-1200 mg.

Formulation 206: adicillin sodium 0.5-4 g, potassium clavulanate 0.05-5 g, disodium EDTA 0.1-100 mg, sodium citrate 10-5000 mg, and citric acid 20-1200 mg.

Formulation 207: ampicillin sodium 0.5-4 g, potassium clavulanate 0.05-5 g, disodium EDTA 0.1-100 mg, sodium citrate 10-5000 mg, and citric acid 20-1200 mg.

Formulation 208: amoxicillin sodium 0.5-4 g, potassium clavulanate 0.05-5 g, disodium EDTA 0.1-100 mg, sodium citrate 10-5000 mg, and citric acid 20-1200 mg.

Formulation 209: ticarcillin sodium 0.5-4 g, potassium clavulanate 0.05-5 g, disodium EDTA 0.1-100 mg, sodium citrate 10-5000 mg, and citric acid 20-1200 mg.

Formulation 210: carbenicillin sodium 0.5-4 g, potassium clavulanate 0.05-5 g, disodium EDTA 0.1-100 mg, sodium citrate 10-5000 mg, and citric acid 20-1200 mg.

Formulation 211: sulbenicillin sodium 0.5-4 g, potassium clavulanate 0.05-5 g, disodium EDTA 0.1-100 mg, sodium citrate 10-5000 mg, and citric acid 20-1200 mg.

Formulation 212: hetacillin sodium 0.5-4 g, potassium clavulanate 0.05-5 g, disodium EDTA 0.1-100 mg, sodium citrate 10-5000 mg, and citric acid 20-1200 mg.

Formulation 213: apalcillin sodium 0.5-4 g, potassium clavulanate 0.05-5 g, disodium EDTA 0.1-100 mg, sodium citrate 10-5000 mg, and citric acid 20-1200 mg.

Formulation 214: mezlocillin sodium 0.5-4 g, potassium clavulanate 0.05-5 g, disodium EDTA 0.1-100 mg, sodium citrate 10-5000 mg, and citric acid 20-1200 mg.

Formulation 215: temocillin sodium 0.5-4 g, potassium clavulanate 0.05-5 g, disodium EDTA 0.1-100 mg, sodium citrate 10-5000 mg, and citric acid 20-1200 mg.

Formulation 216: formidacillin sodium 0.5-4 g, potassium clavulanate 0.05-5 g, disodium EDTA 0.1-100 mg, sodium citrate 10-5000 mg, and citric acid 20-1200 mg.

Formulation 217: aspoxicillin sodium 0.5-4 g, potassium clavulanate 0.05-5 g, disodium EDTA 0.1-100 mg, sodium citrate 10-5000 mg, and citric acid 20-1200 mg.

Formulation 218: lenampicillin sodium 0.5-4 g, potassium clavulanate 0.05-5 g, disodium EDTA 0.1-100 mg, sodium citrate 10-5000 mg, and citric acid 20-1200 mg.

Formulation 219: cefbuperazone sodium 0.5-4 g, and disodium EDTA 0.1-100 mg.

Formulation 220: cefotetan sodium 0.5-4 g, and disodium EDTA 0.1-100 mg.

Formulation 221: latamoxef sodium 0.5-4 g, and disodium EDTA 0.1-100 mg.

Formulation 222: flomoxef sodium 0.5-4 g, and disodium EDTA 0.1-100 mg.

Formulation 223: loracarbef sodium 0.5-4 g, and disodium EDTA 0.1-100 mg.

Formulation 224: cefinetazol sodium 0.5-4 g, and disodium EDTA 0.1-100 mg.

Formulation 225: cefoxitin sodium 0.5-4 g, and disodium EDTA 0.1-100 mg.

Formulation 226: cefclidin sodium 0.5-4 g, and disodium EDTA 0.1-100 mg.

Formulation 227: cefpirome sodium 0.5-4 g, and disodium EDTA 0.1-100 mg.

Formulation 228: cephalosporin sodium 0.5-4 g, and disodium EDTA 0.1-100 mg.

Formulation 229: cefodizime sodium 0.5-4 g, and disodium EDTA 0.1-100 mg.

Formulation 230: ceftibuten sodium 0.5-4 g, and disodium EDTA 0.1-100 mg.

Formulation 231: ceftazidime sodium 0.5-4 g, and disodium EDTA 0.1-100 mg.

Formulation 232: cefixime sodium 0.5-4 g, and disodium EDTA 0.1-100 mg.

Formulation 233: cefuzonam sodium 0.5-4 g, and disodium EDTA 0.1-100 mg.

Formulation 234: ceftriaxone sodium 0.5-4 g, and disodium EDTA 0.1-100 mg.

Formulation 235: ceftizoxime sodium 0.5-4 g, and disodium EDTA 0.1-100 mg.

Formulation 236: cefmenoxime sodium 0.5-4 g, and disodium EDTA 0.1-100 mg.

Formulation 237: cefalothine sodium 0.5-4 g, and disodium EDTA 0.1-100 mg.

Formulation 238: cefotaxime sodium 0.5-4 g, and disodium EDTA 0.1-100 mg.

Formulation 239: cefuroxime sodium 0.5-4 g, and disodium EDTA 0.1-100 mg.

Formulation 240: Cefoperazone sodium 0.5-4 g, and disodium EDTA 0.1-100 mg.

Formulation 241: cefsulodin sodium 0.5-4 g, and disodium EDTA 0.1-100 mg.

Formulation 242: cefamandole sodium 0.5-4 g, and disodium EDTA 0.1-100 mg.

Formulation 243: cefadroxil sodium 0.5-4 g, and disodium EDTA 0.1-100 mg.

Formulation 244: cefaclor sodium 0.5-4 g, and disodium EDTA 0.1-100 mg.

Formulation 245: cefalexin sodium 0.5-4 g, and disodium EDTA 0.1-100 mg.

Formulation 246: cefaloglycin sodium 0.5-4 g, and disodium EDTA 0.1-100 mg.

Formulation 247: cefapirin sodium 0.5-4 g, and disodium EDTA 0.1-100 mg.

Formulation 248: cefazolin sodium 0.5-4 g, and disodium EDTA 0.1-100 mg.

Formulation 249: pheneticillin sodium 0.5-4 g, tazobactam sodium 0.05-5 g, disodium EDTA 0.1-100 mg, amikacin sulfate 0.05-4 g, sodium citrate 10-5000 mg, and citric acid 20-1200 mg.

Formulation 250: propicillin sodium 0.5-4 g, tazobactam sodium 0.05-5 g, disodium EDTA 0.1-100 mg, amikacin sulfate 0.05-4 g, sodium citrate 10-5000 mg, and citric acid 20-1200 mg.

Formulation 251: azidocillin sodium 0.5-4 g, tazobactam sodium 0.05-5 g, disodium EDTA 0.1-100 mg, amikacin sulfate 0.05-4 g, sodium citrate 10-5000 mg, and citric acid 20-1200 mg.

Formulation 252: trityl penicillin sodium 0.5-4 g, tazobactam sodium 0.05-5 g, disodium EDTA 0.1-100 mg, amikacin sulfate 0.05-4 g, sodium citrate 10-5000 mg, and citric acid 20-1200 mg.

Formulation 253: methicillin sodium 0.5-4 g, tazobactam sodium 0.05-5 g, disodium EDTA 0.1-100 mg, amikacin sulfate 0.05-4 g, sodium citrate 10-5000 mg, and citric acid 20-1200 mg.

Formulation 254: nafcillin sodium 0.5-4 g, tazobactam sodium 0.05-5 g, disodium EDTA 0.1-100 mg, amikacin sulfate 0.05-4 g, and sodium citrate 0.01-5 g.

Formulation 255: oxacillin sodium 0.5-4 g, tazobactam sodium 0.05-5 g, disodium EDTA 0.1-100 mg, amikacin sulfate 0.05-4 g, and sodium citrate 0.01-5 g.

Formulation 256: cloxacillin sodium 0.5-4 g, tazobactam sodium 0.05-5 g, disodium EDTA 0.1-100 mg, amikacin sulfate 0.05-4 g, and sodium citrate 0.01-5 g.

Formulation 257: dicloxacillin sodium 0.5-4 g, tazobactam sodium 0.05-5 g, disodium EDTA 0.1-100 mg, amikacin sulfate 0.05-4 g, and sodium citrate 0.01-5 g.

Formulation 258: flucloxacillin sodium 0.5-4 g, tazobactam sodium 0.05-5 g, disodium EDTA 0.1-100 mg, amikacin sulfate 0.05-4 g, and sodium citrate 0.01-5 g.

Formulation 259: mecillinam sodium 0.5-4 g, tazobactam sodium 0.05-5 g, disodium EDTA 0.1-100 mg, amikacin sulfate 0.05-4 g, and sodium citrate 0.01-5 g.

Formulation 260: adicillin sodium 0.5-4 g, tazobactam sodium 0.05-5 g, disodium EDTA 0.1-100 mg, amikacin sulfate 0.05-4 g, and sodium citrate 0.01-5 g.

Formulation 261: ampicillin sodium 0.5-4 g, tazobactam sodium 0.05-5 g, disodium EDTA 0.1-100 mg, amikacin sulfate 0.05-4 g, and sodium citrate 0.01-5 g.

Formulation 262: amoxicillin sodium 0.5-4 g, tazobactam sodium 0.05-5 g, disodium EDTA 0.1-100 mg, amikacin sulfate 0.05-4 g, and sodium citrate 0.01-5 g.

Formulation 263: ticarcillin sodium 0.5-4 g, tazobactam sodium 0.05-5 g, disodium EDTA 0.1-100 mg, amikacin sulfate 0.05-4 g, and sodium citrate 0.01-5 g.

Formulation 264: carbenicillin sodium 0.5-4 g, tazobactam sodium 0.05-5 g, disodium EDTA 0.1-100 mg, amikacin sulfate 0.05-4 g, and sodium citrate 0.01-5 g.

Formulation 265: sulbenicillin sodium 0.5-4 g, tazobactam sodium 0.05-5 g, disodium EDTA 0.1-100 mg, amikacin sulfate 0.05-4 g, and sodium citrate 0.01-5 g.

Formulation 266: hetacillin sodium 0.5-4 g, tazobactam sodium 0.05-5 g, disodium EDTA 0.1-100 mg, amikacin sulfate 0.05-4 g, and sodium citrate 0.01-5 g.

Formulation 267: apalcillin sodium 0.5-4 g, tazobactam sodium 0.05-5 g, disodium EDTA 0.1-100 mg, amikacin sulfate 0.05-4 g, and sodium citrate 0.01-5 g.

Formulation 268: mezlocillin sodium 0.5-4 g, tazobactam sodium 0.05-5 g, disodium EDTA 0.1-100 mg, amikacin sulfate 0.05-4 g, and sodium citrate 0.01-5 g.

Formulation 269: temocillin sodium 0.5-4 g, tazobactam sodium 0.05-5 g, disodium EDTA 0.1-100 mg, amikacin sulfate 0.05-4 g, and sodium citrate 0.01-5 g.

Formulation 270: formidacillin sodium 0.5-4 g, tazobactam sodium 0.05-5 g, disodium EDTA 0.1-100 mg, amikacin sulfate 0.05-4 g, and sodium citrate 0.01-5 g.

Formulation 271: aspoxicillin sodium 0.5-4 g, tazobactam sodium 0.05-5 g, disodium EDTA 0.1-100 mg, amikacin sulfate 0.05-4 g, and sodium citrate 0.01-5 g.

Formulation 272: lenampicillin sodium 0.5-4 g, tazobactam sodium 0.05-5 g, disodium EDTA 0.1-100 mg, amikacin sulfate 0.05-4 g, and sodium citrate 0.01-5 g.

Formulation 273: pheneticillin sodium 0.5-4 g, tazobactam sodium 0.05-5 g, disodium EDTA 0.1-100 mg, gentamicin sulfate 0.05-4 g, and sodium citrate 0.01-5 g.

Formulation 274: propicillin sodium 0.5-4 g, tazobactam sodium 0.05-5 g, disodium EDTA 0.1-100 mg, gentamicin sulfate 0.05-4 g, and sodium citrate 0.01-5 g.

Formulation 275: azidocillin sodium 0.5-4 g, tazobactam sodium 0.05-5 g, disodium EDTA 0.1-100 mg, gentamicin sulfate 0.05-4 g, and sodium citrate 0.01-5 g.

Formulation 276: trityl penicillin sodium 0.5-4 g, tazobactam sodium 0.05-5 g, disodium EDTA 0.1-100 mg, gentamicin sulfate 0.05-4 g, sodium citrate 0.01-5 g, and citric acid 20-1200 mg.

Formulation 277: methicillin sodium 0.5-4 g, tazobactam sodium 0.05-5 g, disodium EDTA 0.1-100 mg, gentamicin sulfate 0.05-4 g, sodium citrate 0.01-5 g, and citric acid 20-1200 mg.

Formulation 278: nafcillin sodium 0.5-4 g, tazobactam sodium 0.05-5 g, disodium EDTA 0.1-100 mg, gentamicin sulfate 0.05-4 g, and sodium citrate 0.01-5 g.

Formulation 279: oxacillin sodium 0.5-4 g, tazobactam sodium 0.05-5 g, disodium EDTA 0.1-100 mg, gentamicin sulfate 0.05-4 g, and sodium citrate 0.01-5 g.

Formulation 280: cloxacillin sodium 0.5-4 g, tazobactam sodium 0.05-5 g, disodium EDTA 0.1-100 mg, gentamicin sulfate 0.05-4 g, and sodium citrate 0.01-5 g.

Formulation 281: dicloxacillin sodium 0.5-4 g, tazobactam sodium 0.05-5 g, disodium EDTA 0.1-100 mg, gentamicin sulfate 0.05-4 g, and sodium citrate 0.01-5 g.

Formulation 282: flucloxacillin sodium 0.5-4 g, tazobactam sodium 0.05-5 g, disodium EDTA 0.1-100 mg, gentamicin sulfate 0.05-4 g, and sodium citrate 0.01-5 g.

Formulation 283: mecillinam sodium 0.5-4 g, tazobactam sodium 0.05-5 g, disodium EDTA 0.1-100 mg, gentamicin sulfate 0.05-4 g, and sodium citrate 0.01-5 g.

Formulation 284: adicillin sodium 0.5-4 g, tazobactam sodium 0.05-5 g, disodium EDTA 0.1-100 mg, gentamicin sulfate 0.05-4 g, and sodium citrate 0.01-5 g.

Formulation 285: ampicillin sodium 0.5-4 g, tazobactam sodium 0.05-5 g, disodium EDTA 0.1-100 mg, gentamicin sulfate 0.05-4 g, and sodium citrate 0.01-5 g.

Formulation 286: amoxicillin sodium 0.5-4 g, tazobactam sodium 0.05-5 g, disodium EDTA 0.1-100 mg, gentamicin sulfate 0.05-4 g, and sodium citrate 0.01-5 g.

Formulation 287: ticarcillin sodium 0.5-4 g, tazobactam sodium 0.05-5 g, disodium EDTA 0.1-100 mg, gentamicin sulfate 0.05-4 g, and sodium citrate 0.01-5 g.

Formulation 288: carbenicillin sodium 0.5-4 g, tazobactam sodium 0.05-5 g, disodium EDTA 0.1-100 mg, gentamicin sulfate 0.05-4 g, and sodium citrate 0.01-5 g.

Formulation 289: sulbenicillin sodium 0.5-4 g, tazobactam sodium 0.05-5 g, disodium EDTA 0.1-100 mg, gentamicin sulfate 0.05-4 g, and sodium citrate 0.01-5 g.

Formulation 290: hetacillin sodium 0.5-4 g, tazobactam sodium 0.05-5 g, disodium EDTA 0.1-100 mg, gentamicin sulfate 0.05-4 g, and sodium citrate 0.01-5 g.

Formulation 291: apalcillin sodium 0.5-4 g, tazobactam sodium 0.05-5 g, disodium EDTA 0.1-100 mg, gentamicin sulfate 0.05-4 g, and sodium citrate 0.01-5 g.

Formulation 292: mezlocillin sodium 0.5-4 g, tazobactam sodium 0.05-5 g, disodium EDTA 0.1-100 mg, gentamicin sulfate 0.05-4 g, and sodium citrate 0.01-5 g.

Formulation 293: temocillin sodium 0.5-4 g, tazobactam sodium 0.05-5 g, disodium EDTA 0.1-100 mg, gentamicin sulfate 0.05-4 g, and sodium citrate 0.01-5 g.

Formulation 294: formidacillin sodium 0.5-4 g, tazobactam sodium 0.05-5 g, disodium EDTA 0.1-100 mg, gentamicin sulfate 0.05-4 g, and sodium citrate 0.01-5 g.

Formulation 295: aspoxicillin sodium 0.5-4 g, tazobactam sodium 0.05-5 g, disodium EDTA 0.1-100 mg, gentamicin sulfate 0.05-4 g, and sodium citrate 0.01-5 g.

Formulation 296: lenampicillin sodium 0.5-4 g, tazobactam sodium 0.05-5 g, disodium EDTA 0.1-100 mg, gentamicin sulfate 0.05-4 g, and sodium citrate 0.01-5 g.

Formulation 297: pheneticillin sodium 0.5-4 g, tazobactam sodium 0.05-5 g, disodium EDTA 0.1-100 mg, etimicin sulfate 0.05-4 g, and sodium citrate 0.01-5 g.

Formulation 298: propicillin sodium 0.5-4 g, tazobactam sodium 0.05-5 g, disodium EDTA 0.1-100 mg, etimicin sulfate 0.05-4 g, and sodium citrate 0.01-5 g.

Formulation 299: azidocillin sodium 0.5-4 g, tazobactam sodium 0.05-5 g, disodium EDTA 0.1-100 mg, etimicin sulfate 0.05-4 g, and sodium citrate 0.01-5 g.

Formulation 300: trityl penicillin sodium 0.5-4 g, tazobactam sodium 0.05-5 g, disodium EDTA 0.1-100 mg, etimicin sulfate 0.05-4 g, and sodium citrate 0.01-5 g.

Formulation 301: methicillin sodium 0.5-4 g, tazobactam sodium 0.05-5 g, disodium EDTA 0.1-100 mg, etimicin sulfate 0.05-4 g, and sodium citrate 0.01-5 g.

Formulation 302: nafcillin sodium 0.5-4 g, tazobactam sodium 0.05-5 g, disodium EDTA 0.1-100 mg, etimicin sulfate 0.05-4 g, and sodium citrate 0.01-5 g.

Formulation 303: oxacillin sodium 0.5-4 g, tazobactam sodium 0.05-5 g, disodium EDTA 0.1-100 mg, etimicin sulfate 0.05-4 g, and sodium citrate 0.01-5 g.

Formulation 304: cloxacillin sodium 0.5-4 g, tazobactam sodium 0.05-5 g, disodium EDTA 0.1-100 mg, etimicin sulfate 0.05-4 g, and sodium citrate 0.01-5 g.

Formulation 305: dicloxacillin sodium 0.5-4 g, tazobactam sodium 0.05-5 g, disodium EDTA 0.1-100 mg, etimicin sulfate 0.05-4 g, and sodium citrate 0.01-5 g.

Formulation 306: flucloxacillin sodium 0.5-4 g, tazobactam sodium 0.05-5 g, disodium EDTA 0.1-100 mg, etimicin sulfate 0.05-4 g, and sodium citrate 0.01-5 g.

Formulation 307: mecillinam sodium 0.5-4 g, tazobactam sodium 0.05-5 g, disodium EDTA 0.1-100 mg, etimicin sulfate 0.05-4 g, and sodium citrate 0.01-5 g.

Formulation 308: adicillin sodium 0.5-4 g, tazobactam sodium 0.05-5 g, disodium EDTA 0.1-100 mg, etimicin sulfate 0.05-4 g, and sodium citrate 0.01-5 g.

Formulation 309: ampicillin sodium 0.5-4 g, tazobactam sodium 0.05-5 g, disodium EDTA 0.1-100 mg, etimicin sulfate 0.05-4 g, and sodium citrate 0.01-5 g.

Formulation 310: amoxicillin sodium 0.5-4 g, tazobactam sodium 0.05-5 g, disodium EDTA 0.1-100 mg, etimicin sulfate 0.05-4 g, and sodium citrate 0.01-5 g.

Formulation 311: ticarcillin sodium 0.5-4 g, tazobactam sodium 0.05-5 g, disodium EDTA 0.1-100 mg, etimicin sulfate 0.05-4 g, and sodium citrate 0.01-5 g.

Formulation 312: carbenicillin sodium 0.5-4 g, tazobactam sodium 0.05-5 g, disodium EDTA 0.1-100 mg, etimicin sulfate 0.05-4 g, and sodium citrate 0.01-5 g.

Formulation 313: sulbenicillin sodium 0.5-4 g, tazobactam sodium 0.05-5 g, disodium EDTA 0.1-100 mg, etimicin sulfate 0.05-4 g, and sodium citrate 0.01-5 g.

Formulation 314: hetacillin sodium 0.5-4 g, tazobactam sodium 0.05-5 g, disodium EDTA 0.1-100 mg, etimicin sulfate 0.05-4 g, and sodium citrate 0.01-5 g.

Formulation 315: apalcillin sodium 0.5-4 g, tazobactam sodium 0.05-5 g, disodium EDTA 0.1-100 mg, etimicin sulfate 0.05-4 g, and sodium citrate 0.01-5 g.

Formulation 316: mezlocillin sodium 0.5-4 g, tazobactam sodium 0.05-5 g, disodium EDTA 0.1-100 mg, etimicin sulfate 0.05-4 g, and sodium citrate 0.01-5 g.

Formulation 317: temocillin sodium 0.5-4 g, tazobactam sodium 0.05-5 g, disodium EDTA 0.1-100 mg, etimicin sulfate 0.05-4 g, and sodium citrate 0.01-5 g.

Formulation 318: formidacillin sodium 0.5-4 g, tazobactam sodium 0.05-5 g, disodium EDTA 0.1-100 mg, etimicin sulfate 0.05-4 g, and sodium citrate 0.01-5 g.

Formulation 319: aspoxicillin sodium 0.5-4 g, tazobactam sodium 0.05-5 g, disodium EDTA 0.1-100 mg, etimicin sulfate 0.05-4 g, and sodium citrate 0.01-5 g.

Formulation 320: lenampicillin sodium 0.5-4 g, tazobactam sodium 0.05-5 g, disodium EDTA 0.1-100 mg, etimicin sulfate 0.05-4 g, and sodium citrate 0.01-5 g.

Formulation 321: pheneticillin sodium 0.5-4 g, and disodium EDTA 0.1-100 mg.

Formulation 322: propicillin sodium 0.5-4 g, and disodium EDTA 0.1-100 mg.

Formulation 323: azidocillin sodium 0.5-4 g, and disodium EDTA 0.1-100 mg.

Formulation 324: trityl penicillin sodium 0.5-4 g, and disodium EDTA 0.1-100 mg.

Formulation 325: methicillin sodium 0.5-4 g, and disodium EDTA 0.1-100 mg.

Formulation 326: nafcillin sodium 0.5-4 g, and disodium EDTA 0.1-100 mg.

Formulation 327: oxacillin sodium 0.5-4 g, and disodium EDTA 0.1-100 mg.

Formulation 328: cloxacillin sodium 0.5-4 g, and disodium EDTA 0.1-100 mg.

Formulation 329: dicloxacillin sodium 0.5-4 g, and disodium EDTA 0.1-100 mg.

Formulation 330: flucloxacillin sodium 0.5-4 g, and disodium EDTA 0.1-100 mg.

Formulation 331: mecillinam sodium 0.5-4 g, and disodium EDTA 0.1-100 mg.

Formulation 332: adicillin sodium 0.5-4 g, and disodium EDTA 0.1-100 mg.

Formulation 333: ampicillin sodium 0.5-4 g, and disodium EDTA 0.1-100 mg.

Formulation 334: amoxicillin sodium 0.5-4 g, and disodium EDTA 0.1-100 mg.

Formulation 335: ticarcillin sodium 0.5-4 g, and disodium EDTA 0.1-100 mg.

Formulation 336: carbenicillin sodium 0.5-4 g, and disodium EDTA 0.1-100 mg.

Formulation 337: sulbenicillin sodium 0.5-4 g, and disodium EDTA 0.1-100 mg.

Formulation 338: hetacillin sodium 0.5-4 g, and disodium EDTA 0.1-100 mg.

Formulation 339: apalcillin sodium 0.5-4 g, and disodium EDTA 0.1-100 mg.

Formulation 340: mezlocillin sodium 0.5-4 g, and disodium EDTA 0.1-100 mg.

Formulation 341: temocillin sodium 0.5-4 g, and disodium EDTA 0.1-100 mg.

Formulation 342: formidacillin sodium 0.5-4 g, and disodium EDTA 0.1-100 mg.

Formulation 343: aspoxicillin sodium 0.5-4 g, and disodium EDTA 0.1-100 mg.

Formulation 344: lenampicillin sodium 0.5-4 g, and disodium EDTA 0.1-100 mg.

Formulation 345: cefbuperazone sodium 0.5-4 g, sulbactam sodium 0.1-5 g, disodium EDTA 0.1-100 mg, sodium citrate 10-5000 mg, and citric acid 20-1200 mg.

Formulation 346: cefotetan sodium 0.5-4 g, sulbactam sodium 0.1-5 g, disodium EDTA 0.1-100 mg, sodium citrate 10-5000 mg, and citric acid 20-1200 mg.

Formulation 347: latamoxef sodium 0.5-4 g, sulbactam sodium 0.1-5 g, disodium EDTA 0.1-100 mg, sodium citrate 10-5000 mg, and citric acid 20-1200 mg.

Formulation 348: flomoxef sodium 0.5-4 g, sulbactam sodium 0.1-5 g, disodium EDTA 0.1-100 mg, sodium citrate 10-5000 mg, and citric acid 20-1200 mg.

Formulation 349: loracarbef sodium 0.5-4 g, sulbactam sodium 0.1-5 g, disodium EDTA 0.1-100 mg, sodium citrate 10-5000 mg, and citric acid 20-1200 mg.

Formulation 350: cefinetazol sodium 0.5-4 g, sulbactam sodium 0.1-5 g, disodium EDTA 0.1-100 mg, sodium citrate 10-5000 mg, and citric acid 20-1200 mg.

Formulation 351: cefoxitin sodium 0.5-4 g, sulbactam sodium 0.1-5 g, disodium EDTA 0.1-100 mg, sodium citrate 10-5000 mg, and citric acid 20-1200 mg.

Formulation 352: cefclidin sodium 0.5-4 g, sulbactam sodium 0.1-5 g, disodium EDTA 0.1-100 mg, sodium citrate 10-5000 mg, and citric acid 20-1200 mg.

Formulation 353: cefpirome sodium 0.5-4 g, sulbactam sodium 0.1-5 g, disodium EDTA 0.1-100 mg, sodium citrate 10-5000 mg, and citric acid 20-1200 mg.

Formulation 354: cephalosporin sodium 0.5-4 g, sulbactam sodium 0.1-5 g, disodium EDTA 0.1-100 mg, sodium citrate 10-5000 mg, and citric acid 20-1200 mg.

Formulation 355: cefodizime sodium 0.5-4 g, sulbactam sodium 0.1-5 g, disodium EDTA 0.1-100 mg, sodium citrate 10-5000 mg, and citric acid 20-1200 mg.

Formulation 356: ceftibuten sodium 0.5-4 g, sulbactam sodium 0.1-5 g, disodium EDTA 0.1-100 mg, sodium citrate 10-5000 mg, and citric acid 20-1200 mg.

Formulation 357: ceftazidime sodium 0.5-4 g, sulbactam sodium 0.1-5 g, disodium EDTA 0.1-100 mg, sodium citrate 10-5000 mg, and citric acid 20-1200 mg.

Formulation 358: cefixime sodium 0.5-4 g, sulbactam sodium 0.1-5 g, disodium EDTA 0.1-100 mg, sodium citrate 10-5000 mg, and citric acid 20-1200 mg.

Formulation 359: cefuzonam sodium 0.5-4 g, sulbactam sodium 0.1-5 g, disodium EDTA 0.1-100 mg, sodium citrate 10-5000 mg, and citric acid 20-1200 mg.

Formulation 360: ceftriaxone sodium 0.5-4 g, sulbactam sodium 0.1-5 g, disodium EDTA 0.1-100 mg, sodium citrate 10-5000 mg, and citric acid 20-1200 mg.

Formulation 361: cefinenoxime sodium 0.5-4 g, sulbactam sodium 0.1-5 g, disodium EDTA 0.1-100 mg, sodium citrate 10-5000 mg, and citric acid 20-1200 mg.

Formulation 362: ceftizoxime sodium 0.5-4 g, sulbactam sodium 0.1-5 g, disodium EDTA 0.1-100 mg, sodium citrate 10-5000 mg, and citric acid 20-1200 mg.

Formulation 363: cefotaxime sodium 0.5-4 g, sulbactam sodium 0.1-5 g, disodium EDTA 0.1-100 mg, sodium citrate 10-5000 mg, and citric acid 20-1200 mg.

Formulation 364: cefuroxime sodium 0.5-4 g, sulbactam sodium 0.1-5 g, disodium EDTA 0.1-100 mg, sodium citrate 10-5000 mg, and citric acid 20-1200 mg.

Formulation 365: Cefoperazone sodium 0.5-4 g, sulbactam sodium 0.1-5 g, disodium EDTA 0.1-100 mg, sodium citrate 10-5000 mg, and citric acid 20-1200 mg.

Formulation 366: cefsulodin sodium 0.5-4 g, sulbactam sodium 0.1-5 g, disodium EDTA 0.1-100 mg, sodium citrate 10-5000 mg, and citric acid 20-1200 mg.

Formulation 367: cefamandole sodium 0.5-4 g, sulbactam sodium 0.1-5 g, disodium EDTA 0.1-100 mg, sodium citrate 10-5000 mg, and citric acid 20-1200 mg.

Formulation 368: cefadroxil sodium 0.5-4 g, sulbactam sodium 0.1-5 g, disodium EDTA 0.1-100 mg, sodium citrate 10-5000 mg, and citric acid 20-1200 mg.

Formulation 369: cefaclor sodium 0.5-4 g, sulbactam sodium 0.1-5 g, disodium EDTA 0.1-100 mg, sodium citrate 10-5000 mg, and citric acid 20-1200 mg.

Formulation 370: cefalexin sodium 0.5-4 g, sulbactam sodium 0.1-5 g, disodium EDTA 0.1-100 mg, sodium citrate 10-5000 mg, and citric acid 20-1200 mg.

Formulation 371: cefaloglycin sodium 0.5-4 g, sulbactam sodium 0.1-5 g, disodium EDTA 0.1-100 mg, sodium citrate 10-5000 mg, and citric acid 20-1200 mg.

Formulation 372: cefapirin sodium 0.5-4 g, sulbactam sodium 0.1-5 g, disodium EDTA 0.1-100 mg, sodium citrate 10-5000 mg, and citric acid 20-1200 mg.

Formulation 373: cefazolin sodium 0.5-4 g, sulbactam sodium 0.1-5 g, disodium EDTA 0.1-100 mg, sodium citrate 10-5000 mg, and citric acid 20-1200 mg.

Formulation 374: cefalothine sodium 0.5-4 g, sulbactam sodium 0.1-5 g, disodium EDTA 0.1-100 mg, sodium citrate 10-5000 mg, and citric acid 20-1200 mg.

Formulation 375: cefbuperazone sodium 0.5-4 g, tazobactam sodium 0.1-5 g, disodium EDTA 0.1-100 mg, sodium citrate 10-5000 mg, and citric acid 20-1200 mg.

Formulation 376: cefotetan sodium 0.5-4 g, tazobactam sodium 0.1-5 g, disodium EDTA 0.1-100 mg, sodium citrate 10-5000 mg, and citric acid 20-1200 mg.

Formulation 377: latamoxef sodium 0.5-4 g, tazobactam sodium 0.1-5 g, disodium EDTA 0.1-100 mg, sodium citrate 10-5000 mg, and citric acid 20-1200 mg.

Formulation 378: flomoxef sodium 0.5-4 g, tazobactam sodium 0.1-5 g, disodium EDTA 0.1-100 mg, sodium citrate 10-5000 mg, and citric acid 20-1200 mg.

Formulation 379: loracarbef sodium 0.5-4 g, tazobactam sodium 0.1-5 g, disodium EDTA 0.1-100 mg, sodium citrate 10-5000 mg, and citric acid 20-1200 mg.

Formulation 380: cefinetazol sodium 0.5-4 g, tazobactam sodium 0.1-5 g, disodium EDTA 0.1-100 mg, sodium citrate 10-5000 mg, and citric acid 20-1200 mg.

Formulation 381: cefoxitin sodium 0.5-4 g, tazobactam sodium 0.1-5 g, disodium EDTA 0.1-100 mg, sodium citrate 10-5000 mg, and citric acid 20-1200 mg.

Formulation 382: cefclidin sodium 0.5-4 g, tazobactam sodium 0.1-5 g, disodium EDTA 0.1-100 mg, sodium citrate 10-5000 mg, and citric acid 20-1200 mg.

Formulation 383: cefpirome sodium 0.5-4 g, tazobactam sodium 0.1-5 g, disodium EDTA 0.1-100 mg, sodium citrate 10-5000 mg, and citric acid 20-1200 mg.

Formulation 384: cephalosporin sodium 0.5-4 g, tazobactam sodium 0.1-5 g, disodium EDTA 0.1-100 mg, sodium citrate 10-5000 mg, and citric acid 20-1200 mg.

Formulation 385: cefodizime sodium 0.5-4 g, tazobactam sodium 0.1-5 g, disodium EDTA 0.1-100 mg, sodium citrate 10-5000 mg, and citric acid 20-1200 mg.

Formulation 386: ceftibuten sodium 0.5-4 g, tazobactam sodium 0.1-5 g, disodium EDTA 0.1-100 mg, sodium citrate 10-5000 mg, and citric acid 20-1200 mg.

Formulation 387: ceftazidime sodium 0.5-4 g, tazobactam sodium 0.1-5 g, disodium EDTA 0.1-100 mg, sodium citrate 10-5000 mg, and citric acid 20-1200 mg.

Formulation 388: cefixime sodium 0.5-4 g, tazobactam sodium 0.1-5 g, disodium EDTA 0.1-100 mg, sodium citrate 10-5000 mg, and citric acid 20-1200 mg.

Formulation 389: cefuzonam sodium 0.5-4 g, tazobactam sodium 0.1-5 g, disodium EDTA 0.1-100 mg, sodium citrate 10-5000 mg, and citric acid 20-1200 mg.

Formulation 390: ceftriaxone sodium 0.5-4 g, tazobactam sodium 0.1-5 g, disodium EDTA 0.1-100 mg, sodium citrate 10-5000 mg, and citric acid 20-1200 mg.

Formulation 391: ceftizoxime sodium 0.5-4 g, tazobactam sodium 0.1-5 g, disodium EDTA 0.1-100 mg, sodium citrate 10-5000 mg, and citric acid 20-1200 mg.

Formulation 392: cefinenoxime sodium 0.5-4 g, tazobactam sodium 0.1-5 g, disodium EDTA 0.1-100 mg, sodium citrate 10-5000 mg, and citric acid 20-1200 mg.

Formulation 393: cefotaxime sodium 0.5-4 g, tazobactam sodium 0.1-5 g, disodium EDTA 0.1-100 mg, sodium citrate 10-5000 mg, and citric acid 20-1200 mg.

Formulation 394: cefuroxime sodium 0.5-4 g, tazobactam sodium 0.1-5 g, disodium EDTA 0.1-100 mg, sodium citrate 10-5000 mg, and citric acid 20-1200 mg.

Formulation 395: Cefoperazone sodium 0.5-4 g, tazobactam sodium 0.1-5 g, disodium EDTA 0.1-100 mg, sodium citrate 10-5000 mg, and citric acid 20-1200 mg.

Formulation 396: cefsulodin sodium 0.5-4 g, tazobactam sodium 0.1-5 g, disodium EDTA 0.1-100 mg, sodium citrate 10-5000 mg, and citric acid 20-1200 mg.

Formulation 397: cefamandole sodium 0.5-4 g, tazobactam sodium 0.1-5 g, disodium EDTA 0.1-100 mg, sodium citrate 10-5000 mg, and citric acid 20-1200 mg.

Formulation 398: cefadroxil sodium 0.5-4 g, tazobactam sodium 0.1-5 g, disodium EDTA 0.1-100 mg, sodium citrate 10-5000 mg, and citric acid 20-1200 mg.

Formulation 399: cefaclor sodium 0.5-4 g, tazobactam sodium 0.1-5 g, disodium EDTA 0.1-100 mg, sodium citrate 10-5000 mg, and citric acid 20-1200 mg.

Formulation 400: cefalexin sodium 0.5-4 g, tazobactam sodium 0.1-5 g, disodium EDTA 0.1-100 mg, sodium citrate 10-5000 mg, and citric acid 20-1200 mg.

Formulation 401: cefaloglycin sodium 0.5-4 g, tazobactam sodium 0.1-5 g, disodium EDTA 0.1-100 mg, sodium citrate 10-5000 mg, and citric acid 20-1200 mg.

Formulation 402: cefapirin sodium 0.5-4 g, tazobactam sodium 0.1-5 g, disodium EDTA 0.1-100 mg, sodium citrate 10-5000 mg, and citric acid 20-1200 mg.

Formulation 403: cefazolin sodium 0.5-4 g, tazobactam sodium 0.1-5 g, disodium EDTA 0.1-100 mg, sodium citrate 10-5000 mg, and citric acid 20-1200 mg.

Formulation 404: cefalothine sodium 0.5-4 g, tazobactam sodium 0.1-5 g, disodium EDTA 0.1-100 mg, sodium citrate 10-5000 mg, and citric acid 20-1200 mg.

Formulation 405: cefbuperazone sodium 0.5-4 g, potassium clavulanate 0.1-5 g, disodium EDTA 0.1-100 mg, sodium citrate 10-5000 mg, and citric acid 20-1200 mg.

Formulation 406: cefotetan sodium 0.5-4 g, potassium clavulanate 0.1-5 g, disodium EDTA 0.1-100 mg, sodium citrate 10-5000 mg, and citric acid 20-1200 mg.

Formulation 407: latamoxef sodium 0.5-4 g, potassium clavulanate 0.1-5 g, disodium EDTA 0.1-100 mg, sodium citrate 10-5000 mg, and citric acid 20-1200 mg.

Formulation 408: flomoxef sodium 0.5-4 g, potassium clavulanate 0.1-5 g, disodium EDTA 0.1-100 mg, sodium citrate 10-5000 mg, and citric acid 20-1200 mg.

Formulation 409: loracarbef sodium 0.5-4 g, potassium clavulanate 0.1-5 g, disodium EDTA 0.1-100 mg, sodium citrate 10-5000 mg, and citric acid 20-1200 mg.

Formulation 410: cefinetazol sodium 0.5-4 g, potassium clavulanate 0.1-5 g, disodium EDTA 0.1-100 mg, sodium citrate 10-5000 mg, and citric acid 20-1200 mg.

Formulation 411: cefoxitin sodium 0.5-4 g, potassium clavulanate 0.1-5 g, disodium EDTA 0.1-100 mg, sodium citrate 10-5000 mg, and citric acid 20-1200 mg.

Formulation 412: cefclidin sodium 0.5-4 g, potassium clavulanate 0.1-5 g, disodium EDTA 0.1-100 mg, sodium citrate 10-5000 mg, and citric acid 20-1200 mg.

Formulation 413: cefpirome sodium 0.5-4 g, potassium clavulanate 0.1-5 g, disodium EDTA 0.1-100 mg, sodium citrate 10-5000 mg, and citric acid 20-1200 mg.

Formulation 414: cephalosporin sodium 0.5-4 g, potassium clavulanate 0.1-5 g, disodium EDTA 0.1-100 mg, sodium citrate 10-5000 mg, and citric acid 20-1200 mg.

Formulation 415: cefodizime sodium 0.5-4 g, potassium clavulanate 0.1-5 g, disodium EDTA 0.1-100 mg, sodium citrate 10-5000 mg, and citric acid 20-1200 mg.

Formulation 416: ceftibuten sodium 0.5-4 g, potassium clavulanate 0.1-5 g, disodium EDTA 0.1-100 mg, sodium citrate 10-5000 mg, and citric acid 20-1200 mg.

Formulation 417: ceftazidime sodium 0.5-4 g, potassium clavulanate 0.1-5 g, disodium EDTA 0.1-100 mg, sodium citrate 10-5000 mg, and citric acid 20-1200 mg.

Formulation 418: cefixime sodium 0.5-4 g, potassium clavulanate 0.1-5 g, disodium EDTA 0.1-100 mg, sodium citrate 10-5000 mg, and citric acid 20-1200 mg.

Formulation 419: cefuzonam sodium 0.5-4 g, potassium clavulanate 0.1-5 g, disodium EDTA 0.1-100 mg, sodium citrate 10-5000 mg, and citric acid 20-1200 mg.

Formulation 420: ceftriaxone sodium 0.5-4 g, potassium clavulanate 0.1-5 g, disodium EDTA 0.1-100 mg, sodium citrate 10-5000 mg, and citric acid 20-1200 mg.

Formulation 421: ceftizoxime sodium 0.5-4 g, potassium clavulanate 0.1-5 g, disodium EDTA 0.1-100 mg, sodium citrate 10-5000 mg, and citric acid 20-1200 mg.

Formulation 422: cefmenoxime sodium 0.5-4 g, potassium clavulanate 0.1-5 g, disodium EDTA 0.1-100 mg, sodium citrate 10-5000 mg, and citric acid 20-1200 mg.

Formulation 423: cefotaxime sodium 0.5-4 g, potassium clavulanate 0.1-5 g, disodium EDTA 0.1-100 mg, sodium citrate 10-5000 mg, and citric acid 20-1200 mg.

Formulation 424: cefuroxime sodium 0.5-4 g, potassium clavulanate 0.1-5 g, disodium EDTA 0.1-100 mg, sodium citrate 10-5000 mg, and citric acid 20-1200 mg.

Formulation 425: azlocillin sodium 0.5-4 g, disodium EDTA 0.1-100 mg, sodium citrate 10-5000 mg, and citric acid 20-1200 mg.

Formulation 426: azlocillin sodium 0.5-4 g, potassium clavulanate 0.1-5 g, disodium EDTA 0.1-100 mg, sodium citrate 10-5000 mg, and citric acid 20-1200 mg.

Formulation 427: azlocillin sodium 0.5-4 g, sulbactam sodium 0.1-5 g, disodium EDTA 0.1-100 mg, sodium citrate 10-5000 mg, and citric acid 20-1200 mg.

Formulation 428: azlocillin sodium 0.5-4 g, tazobactam sodium 0.1-5 g, disodium EDTA 0.1-100 mg, sodium citrate 10-5000 mg, and citric acid 20-1200 mg.

Formulation 429: azlocillin sodium 0.5-4 g, and disodium EDTA 0.1-100 mg.

Formulation 430: azlocillin sodium 0.5-4 g, potassium clavulanate 0.1-5 g, and disodium EDTA 0.1-100 mg.

Formulation 431: azlocillin sodium 0.5-4 g, sulbactam sodium 0.1-5 g, and disodium EDTA 0.1-100 mg.

Formulation 432: azlocillin sodium 0.5-4 g, tazobactam sodium 0.1-5 g, and disodium EDTA 0.1-100 mg.

Formulation 433: azlocillin sodium 0.5-4 g, tazobactam sodium 0.05-5 g, disodium EDTA 0.1-100 mg, gentamicin sulfate 0.05-4 g, and sodium citrate 0.01-5 g.

Formulation 434: azlocillin sodium 0.5-4 g, tazobactam sodium 0.05-5 g, disodium EDTA 0.1-100 mg, etimicin sulfate 0.05-4 g, and sodium citrate 0.01-5 g.

Formulation 435: azlocillin sodium 0.5-4 g, tazobactam sodium 0.05-5 g, disodium EDTA 0.1-100 mg, amikacin sulfate 0.05-4 g, and sodium citrate 0.01-5 g.

Formulation 436: azlocillin sodium 0.5-4 g, tazobactam sodium 0.05-5 g, disodium EDTA 0.1-100 mg, tobramycin sulfate 0.05-4 g, and sodium citrate 0.01-5 g.

Formulation 437: azlocillin sodium 0.5-4 g, sulbactam sodium 0.05-5 g, disodium EDTA 0.1-100 mg, gentamicin sulfate 0.05-4 g, and sodium citrate 0.01-5 g.

Formulation 438: azlocillin sodium 0.5-4 g, sulbactam sodium 0.05-5 g, disodium EDTA 0.1-100 mg, etimicin sulfate 0.05-4 g, and sodium citrate 0.01-5 g.

Formulation 439: azlocillin sodium 0.5-4 g, sulbactam sodium 0.05-5 g, disodium EDTA 0.1-100 mg, amikacin sulfate 0.05-4 g, and sodium citrate 0.01-5 g.

Formulation 440: azlocillin sodium 0.5-4 g, sulbactam sodium 0.05-5 g, disodium EDTA 0.1-100 mg, tobramycin sulfate 0.05-4 g, and sodium citrate 0.01-5 g.

An iso-osmotic solution may be used to prepare a parenteral solution of the pharmaceutical composition described in this invention. The iso-osmotic solution includes but is not limited to a glucose solution, a fructose solution, and normal saline. The unit dose range of glucose, fructose or sodium chloride is between 0.1 g and 20 g; and the concentration range in the parenteral solution is between 0.1% and 10%.

Gentamicin, amikacin, and etimicin were separately mixed each with five β-lactam antibiotics and two β-lactamase inhibitors. The research on stability and intercomponent compatibility of three dosage forms and preservation methods were carried out with. Specifically, solution preparations were prepared by the following three ways: 1) for use immediately after preparation; 2) solution preparation was prepared firstly and stored with cryopreservation; after thawing an aminoglycoside antibiotics was added prior to use; and 3) firstly prepared as solution, freeze-dried, and preserved at low temperature, thereafter redissolved the mixture, and added aminoglycoside antibiotics prior to use.

The contents of the β-lactam antibiotic, β-lactamase inhibitor and aminoglycoside antibiotic were all maintained at levels higher than 90%. In some of the compositions, the contents of the above-mentioned three species were higher than 95%, which meets the technical requirements of clinically applied multi-drug mixtures. In addition, the results show that EDTA can significantly reduce aggregate particle formation in the solution preparations of the compositions described in this invention. As a result, the use of the pharmaceutical composition of the invention by intravenous injection to treat microbial infection has become much safer, while in the meantime, a choice of simultaneous use of β-lactam antibiotics and aminoglycoside antibiotics has been provided. Treatment with the compositions according to this invention will be more effective. More importantly, due to the potential avoidance of drug resistance caused by single type use of antibiotics, first-time-treatment failure can be prevented.

The solution preparation of the pharmaceutical composition prepared for microbial control can be used as parenteral solution, eye drops, nose drops, ear drops, genital duct drops, wash, or external use solution.

The solution preparation of the pharmaceutical composition may be prepared immediately prior to use; or it may be prepared as solution preparation, sealed, frozen preserved, and thawed at room temperature prior to use.

The pharmaceutical composition may be prepared as a solution, injectable powder, or freeze-dried injectable powder and preserved with cold-storage, and re-dissolved into a liquid solution with injectable fluid immediately prior to use.

Still in other aspects of the invention, provided is a method for the preparation of a solution, a freeze-dried injectable powder of the pharmaceutical composition in the present invention, comprising: (a) dissolving a β-lactam antibiotic, a β-lactamase inhibitor, a disodium EDTA and other components of the pharmaceutical composition in injectable water, or in 2.5% injectable fructose aqueous solution, or in 5% normal saline; (b) adjusting the pH value to between 6 and 6.75; and sub-packaging the resultant solution in containers as unit-dose fluids; (c) placing the unit-dose fluids in a freeze-drier; adjusting the temperature of the freeze drier to minus 35° C., and pumping the atmosphere of the freeze drier to below 40 Pa; (d) adjusting the temperature to 3-5° C., and removing water completely; (e) adjusting the temperature of the freeze drier to 40-50° C. and drying the obtained freeze-dried injectable powder; (f) sealing the bottles with sterile seal-capping; and (g) storing below 5° C. in the dark.

Table 1 lists a part of HIAC test results. The results show that EDTA is effective in inhibiting formation of aggregate particles when the pharmaceutical composition is prepared in the form of a liquid solution.

DETAILED DESCRIPTION OF THE EMBODIMENTS

The amounts of β-lactam antibiotics and β-lactamase inhibitor were determined using C18 reverse-phase LC and UV-VIS detector (Tianjin Hemay BioTech Co., Ltd., analysis method No. HM-K-03). The content of aminoglycoside antibiotics was measured using reverse-phase HPLC and evaporation-light-scattering detector (ELSD detector) (Tianjin Hemay BioTech Co., Ltd., analysis method No. HM-K-08). The amount of antibiotic component at each time point was expressed as a percentage with respect to the amount at the initial time. The relative amount of each antibiotic component in the composition at each time point was expressed as peak area ratio with respect to the corresponding peak area of an external standard.

Example 1

Pharmaceutical Composition of Cefoperazone Sodium and Gentamicin

Preparation

Cefoperazone sodium (4 g) was dissolved in 200 mL of injectable water, and gentamicin parenteral solution (80 mg in 2 mL of injectable water) was added. Upon mixing, a large amount of white solid precipitated out of the solution immediately.

Example 2

Pharmaceutical Composition of Cefoperazone Sodium, Gentamicin, Buffer, and Disodium EDTA 40 mg of cefoperazone sodium and 0.01 mg of disodium EDTA were dissolved in 2 mL of various buffer solutions having different pH value and concentration. Then, 20 μL of gentamicin parenteral solution having a concentration of 40 mg/mL was added. The mixture was ultrasonicated for 5 minutes and clarity observed. Clear solutions were obtained, and there was no precipitate generated when the pH value of buffer solution was above 6. The type of buffer solution used had little effect on the results. The results are shown in the table below.

| Buffer solution | pH of buffer solution | Concentration of buffer solution (mM) | Result |
|---|---|---|---|
| Citric acid/sodium citrate | 5 | 10 | *** |
| Citric acid/sodium citrate | 5.5 | 10 | ** |
| Citric acid/sodium citrate | 6 | 10 | * |
| Citric acid/sodium citrate | 6.5 | 10 | OK |
| Citric acid/sodium citrate | 7.0 | 10 | OK |
| Citric acid/sodium citrate | 7.5 | 10 | OK |
| Citric acid/sodium citrate | 6 | 20 | OK |
| Acetic acid/sodium acetate | 6.5 | 20 | OK |
| Phosphoric acid/disodium hydrogen phosphate | 6.5 | 20 | OK |
| Arginine/arginine sodium | 6.5 | 20 | OK |

* the solution turned slightly turbid,
** the solution turned turbid,
*** the solution turned fairly turbid,
OK: clear solution

Example 3

Pharmaceutical Composition of Cefoperazone Sodium, Sulbactam Sodium, Gentamicin, Buffer, and Disodium EDTA 40 mg of cefoperazone sodium, 0.01 mg of disodium EDTA, and 10 mg of sulbactam sodium were dissolved in 2 mL of various buffer solutions having different pH values and concentration. Then, 20 μL of gentamicin parenteral solution having a concentration of 40 mg/mL was added. The mixture was ultrasonicated for 5 minutes and clarity observed. Clear solutions were obtained, and there was no precipitate generated when the pH value of buffer solution was above 6 and the concentration was higher than 20 mM. The type of buffer solution had little effect on the results. The results are shown in the table below.

| Buffer solution | pH of buffer solution | Concentration of buffer solutions (mM) | Results |
|---|---|---|---|
| Citric acid/sodium citrate | 5.5 | 10 | ** |
| Citric acid/sodium citrate | 6 | 10 | * |
| Citric acid/sodium citrate | 6.5 | 10 | OK |
| Citric acid/sodium citrate | 7.0 | 10 | OK |
| Citric acid/sodium citrate | 7.5 | 10 | OK |
| Citric acid/sodium citrate | 6 | 20 | OK |

* the solution turned slightly turbid,
** the solution turned turbid,
*** the solution turned fairly turbid,
OK: clear solution Example 4

Pharmaceutical Composition of Cefoperazone Sodium, Sulbactam Sodium, Gentamicin, and Sodium Citrate Preparation 0.20 g of sodium citrate was dissolved in 200 mL of injectable water, and the pH value was adjusted to 6.75 with citric acid/sodium hydroxide buffer. Cefoperazone sodium (4 g) and sulbactam sodium (0.5 g) were added, and shaken. Then, gentamicin parenteral solution (80 mg/2 mL) was added dropwise, and small amount of white floc was generated. After 15 min of ultrasonication, the white floc had dissolved to give a clear solution. The solution was packaged in a bottle or a bag and stored at room temperature. HIAC data at 1 and 20 hours were determined (see Table 1). Observation of the appearance of the solution was conducted at 0, 1, 2, 4, and 6 hours. The amounts of cefoperazone sodium and sulbactam sodium were determined by sampling at the above-mentioned time points, and the results are shown below:

| | Time (h) | | | | |
|---|---|---|---|---|---|
| | 0 | 1 | 2 | 4 | 6 |
| Cefoperazone sodium | 101.4 | 98.66 | 98.79 | 101.5 | 107.4 |
| Sulbactam sodium | 101.4 | 101.4 | 101.5 | 109.7 | 103.2 |

Example 5

Pharmaceutical Composition of Cefoperazone Sodium, Sulbactam Sodium, Gentamicin, Sodium Citrate, and Disodium EDTA Preparation Sodium citrate (0.20 g) was dissolved in 200 mL of injectable water, and the pH value was adjusted to 6.75 with citric acid/sodium hydroxide buffer. Cefoperazone sodium (4 g), sulbactam sodium (0.5 g), and disodium EDTA (1 mg) were added and the solution was shaken. Gentamicin parenteral solution (80 mg in 2 mL) was added dropwise, and a small amount of white floc has precipitated out. After 15 min of ultrasonication, the white floc had dissolved to give a clear solution. The solution was packaged in a bottle or a bag and stored at room temperature. HIAC data at 1 and 20 hours were determined (vide infra, Table 1). Observation of the appearance of the solution was conducted at 0, 1, 2, 4, and 6 hours. The amounts of cefoperazone sodium, sulbactam sodium, and gentamicin were determined by sampling at the above-mentioned time points, and the results are shown below:

| | Time (h) | | | | |
|---|---|---|---|---|---|
| | 0 | 1 | 2 | 4 | 6 |
| Cefoperazone sodium | 101.4 | 98.66 | 98.79 | 101.5 | 107.4 |
| Sulbactam sodium | 101.4 | 101.4 | 101.5 | 109.7 | 103.2 |
| Gentamicin | 101.7 | 104.2 | 96.1 | 100.1 | NA |

NA: undetermined content

Example 6

Pharmaceutical Composition of Cefoperazone Sodium, Sulbactam Sodium, Etimicin, Sodium Citrate, and Disodium EDTA Preparation Sodium citrate (0.20 g) was dissolved in 200 mL of injectable water, and the pH value was adjusted to 6.5 with citric acid/sodium hydroxide buffer. Cefoperazone sodium (4 g), sulbactam sodium (1 g), and disodium EDTA (1 mg) were then added and shaken. Etimicin sulfate (200 mg) in the form of parenteral solution was added dropwise, and small amount of white floc had formed generated. After 15 min of ultrasonication, the white floc had dissolved to give a clear solution. The solution was packaged in a bottle or a bag and stored at room temperature. Observation of the appearance of precipitate was conducted at 0, 1, 2, 4, 6 and 8 hours. The amounts of cefoperazone sodium, sulbactam sodium, and etimicin were determined by sampling at the above-mentioned time points, and the results are shown below:

| | Time (h) | | | | | |
|---|---|---|---|---|---|---|
| | 0 | 1 | 2 | 4 | 6 | 8 |
| Cefoperazone sodium | 110.4 | 99.48 | 101.3 | 98.66 | 98.02 | 99.30 |
| Sulbactam sodium | 99.62 | 100.4 | 100.2 | 100.2 | NA | NA |
| Etimicin | 108.9 | 100.2 | 100.5 | 100.4 | 100.4 | 97.50 |

NA: undetermined content

Example 7

Pharmaceutical Composition of Ceftriaxone Sodium, Sulbactam Sodium, Gentamicin Sulfate, Sodium Citrate, and Disodium EDTA Preparation Sodium citrate (0.20 g) was dissolved in 200 mL of injectable water, and the pH value was adjusted to 6.75 with citric acid/sodium hydroxide buffer. Ceftriaxone sodium (2 g), sulbactam sodium (2 g), and disodium EDTA (1 mg) were added and the solution was shaken. Gentamicin sulfate, 80 mg/2 mL parenteral solution, was added dropwise, and a small amount of white floc had formed. After 15 min of ultrasonication, the white floc had dissolved to give a clear solution. The solution was packaged in a bottle or a bag and stored at room temperature. Observation of the appearance of the solution was conducted at 0, 1, 2, 4, and 6 hours. The amounts of ceftriaxone sodium and sulbactam sodium were determined by sampling at the above-mentioned time points, and the results are shown below:

|  | Time (h) | | | | | |
| --- | --- | --- | --- | --- | --- | --- |
|  | 0 | 1 | 2 | 4 | 6 | 8 |
| Ceftriaxone sodium | 97.01 | 100.3 | 96.40 | 99.01 | 98.91 | 99.53 |
| Sulbactam sodium | 96.84 | 94.43 | 93.35 | 93.23 | 92.13 | 93.38 |

Example 8

Pharmaceutical Composition of Ceftriaxone Sodium, Tazobactam Sodium, Gentamicin Sulfate, Sodium Citrate, and Disodium EDTA Preparation Sodium citrate (0.20 g) was dissolved in 200 mL of injectable water, and the pH value was adjusted to 6.75 with citric acid/sodium hydroxide buffer. Ceftriaxone sodium (1 g) tazobactam sodium (1 g) and disodium EDTA (1 mg) were added and the mixture was shaken. Gentamicin sulfate parenteral solution (80 mg in 2 mL) was added dropwise, and small amount of white floc has precipitated out. After 15 min of ultrasonication, the white floc had dissolved to give a clear solution.

100 mL of the resultant solution was filtrated into a container and placed into a freeze drier. The freeze-drier temperature was adjusted to minus 35° C., and the atmosphere of the freeze-drier was pumped to 30 Pa. After removal of water at 3° C., the temperature of the freeze-drier was adjusted to 40° C. to obtain freeze-dried injectable powder. Dry nitrogen was charged and the container was sealed with a sterile cover, and stored in a refrigerator at 0° C. After 7 days, the freeze-dried injectable powder was prepared as solution by mixing with 100 mL of injectable water. Observation of the appearance of precipitate was conducted at 0, 1, 2, 4, 6 and 8 hours. The amounts of ceftriaxone sodium and tazobactam sodium in the solution were determined, and the results are shown below:

|  | Time (h) | | | | | |
| --- | --- | --- | --- | --- | --- | --- |
|  | 0 | 1 | 2 | 4 | 6 | 8 |
| Ceftriaxone sodium | 98.75 | 100.1 | 99.97 | 98.87 | 99.27 | 100.5 |
| Tazobactam sodium | 102.2 | 97.53 | 94.16 | 94.58 | 95.45 | 94.44 |

Example 9

Pharmaceutical Composition of Ceftriaxone Sodium, Etimicin Sulfate, Sodium Citrate, Buffer, and Disodium EDTA Preparation Sodium citrate (0.20 g) was dissolved in 200 mL of injectable water, and the pH value was adjusted to 6.75 with citric acid/sodium hydroxide buffer. Ceftriaxone sodium (4 g) and disodium EDTA (1 mg) were added and shaken. Etimicin sulfate (200 mg) was added dropwise, and a small amount of white floc was generated. After 15 min of ultrasonication, the white floc had dissolved to give a clear solution.

100 mL of the resultant solution was filtrated into a container and placed into a freeze drier. The freeze-drier temperature was adjusted to minus 35° C. and the atmosphere of the freeze-dried was pumped to 30 Pa. After removal of water at 3° C., the temperature of the freeze-drier was adjusted to 40° C. to obtain freeze-dried injectable powder. Dry nitrogen was charged and the container was sealed with a sterile cover, and stored in a refrigerator at 0° C. After 7 days, the freeze-dried injectable powder was prepared as solution by mixing with 100 mL of injectable water. Observation of the appearance of precipitate was conducted at 0, 1, 2, 4, 6 and 8 hours. The amount of ceftriaxone sodium in the solution were determined, and the results are shown below:

|  | Time (h) | | | | | |
| --- | --- | --- | --- | --- | --- | --- |
|  | 0 | 1 | 2 | 4 | 6 | 8 |
| Ceftriaxone sodium | 92.24 | 96.28 | 94.97 | 94.20 | 97.91 | 93.23 |

Example 10

Pharmaceutical Composition of Cefodizime Sodium, Etimicin Sulfate, Sodium Citrate, and Disodium EDTA Preparation Sodium citrate (0.20 g) was dissolved in 200 mL of injectable water, and the pH was adjusted to 6.5 with citric acid. Cefodizime sodium (4 g) and disodium EDTA (1 mg) were added, and the mixture was shaken. Etimicin sulfate (200 mg), in the form of lyophilized powder, was added dropwise, and small amount of white floc had precipitated out. After 15 min of ultrasonication, the white floc had dissolved to give a clear solution. The solution was sealed and stored at room temperature. Observation of the appearance of the solution was conducted at 0, 1, 2, 4, and 6 hours. The amount of cefodizime sodium was determined, and the results are shown below:

|  | Time (h) | | | | | |
| --- | --- | --- | --- | --- | --- | --- |
|  | 0 | 1 | 2 | 4 | 6 | 8 |
| Cefodizime sodium | 92.06 | 99.84 | 99.73 | 98.64 | 94.27 | 96.48 |

Example 11

Pharmaceutical Composition of Mezlocillin Sodium, Etimicin Sulfate, Sodium Citrate, and Disodium EDTA Preparation Sodium citrate (0.20 g) was dissolved in 200 mL of injectable water, and the pH was adjusted to 6.0 with citric acid. Mezlocillin sodium (4 g) and disodium EDTA (1 mg) were added, and the mixture was shaken. Etimicin sulfate (200 mg) was added dropwise, and small amount of white floc had precipitated out. After 15 min of ultrasonication, the white floc had dissolved to give a clear solution.

100 mL of the resultant solution was filtrated into a container and placed into a freeze drier. The freeze-drier temperature was adjusted to minus 35° C., and the atmosphere of the freeze-dried was pumped to 30 Pa. After removal of water at 3° C., the temperature of the freeze-drier was adjusted to 40° C. to obtain the freeze-dried injectable powder. Dry nitrogen was charged and the container was sealed with sterile cover, and stored in a refrigerator at 0° C. After 7 days, the resultant freeze-dried injectable powder was prepared as solution by mixing with 100 mL of injectable water. Observation of the appearance of the solution was conducted at 0, 1, 2, 4, 6 and 8 hours. The content of mezlocillin sodium was determined, and the results are shown below:

|  | Time (h) | | | | | |
| --- | --- | --- | --- | --- | --- | --- |
|  | 0 | 1 | 2 | 4 | 6 | 8 |
| Mezlocillin sodium | 97.11 | 90.83 | 98.18 | 93.69 | 91.23 | 94.39 |

Example 12

Pharmaceutical Composition of Cefoperazone Sodium, Sulbactam Sodium, Disodium EDTA, and Sodium Citrate Preparation Cefoperazone sodium (4 g), sulbactam sodium (1.0 g), disodium EDTA (1 mg), and sodium citrate (0.20 g) were dissolved in 10 mL of injectable water. The pH value was adjusted to 6.75 with citric acid. A clear solution was obtained after a 10 minute ultrasonication. The resultant solution was filtrated into a container and placed into a freeze drier. The freeze-drier temperature was adjusted to minus 35° C., and the atmosphere of the freeze-drier was pumped to below 40 Pa. After removal of water at 3° C., the temperature of the freeze-drier was adjusted to 40° C. to obtain freeze-dried injectable powder. Dry nitrogen was charged and the container was sealed with sterile cover, and stored in refrigerator at 0° C. After 7 days, the resultant freeze-dried injectable powder was prepared as solution by adding 100 mL of injectable water. Observation of the appearance of the solution was conducted at 0, 1, 2, 4, 6 and 8 hours. The amounts of cefoperazone sodium and sulbactam sodium were determined, and the results are shown below:

|  | Time (h) | | | | | |
| --- | --- | --- | --- | --- | --- | --- |
|  | 0 | 1 | 2 | 4 | 6 | 8 |
| Cefoperazone sodium | 100.2 | 99.0 | 99.0 | 96.2 | 94.5 | 95.3 |
| Sulbactam sodium | 98.5 | 98.7 | 98.2 | 95.6 | 94.0 | 96.1 |

Example 13

Pharmaceutical Composition of Cefoperazone Sodium, Sulbactam Sodium, Disodium EDTA, Etimicin Sulfate, and Sodium Citrate 20 mg of etimicin sulfate was added to 10 mL of the clear solution prepared from the freeze-dried injectable powder of Example 12. After 10 min of ultrasonication, the white floc had dissolved to give a clear solution. Observation of the appearance of the solution was conducted at 0, 1, 2, 4, 6 and 8 hours. The amounts of cefoperazone sodium and etimicin were determined, and the results are shown below:

|  | Time (h) | | | | | |
| --- | --- | --- | --- | --- | --- | --- |
|  | 0 | 1 | 2 | 4 | 6 | 8 |
| Cefoperazone sodium | 100.2 | 99.0 | 99.0 | 96.2 | 94.5 | 95.3 |
| Etimicin | 100 | 98.8 | 97.5 | 98.4 | 95.6 | 92.8 |

Example 14

Pharmaceutical Composition of Cefoperazone Sodium, Sulbactam Sodium, Disodium EDTA, Sodium Citrate, and Gentamicin Sulfate Preparation Sodium citrate (0.20 g) was dissolved in 200 mL of injectable water, and the pH value was adjusted to 6.5 with citric acid/sodium hydroxide buffer. Cefoperazone sodium (4 g), sulbactam sodium (2 g), and sodium EDTA (1 mg) were then added, and the mixture was shaken. Gentamicin (160 mg/2 mL, parenteral solution) was added dropwise, and a small amount of white floc had precipitated out. After 15 min of ultrasonication, the white floc had dissolved to give a clear solution. The solution was sealed and stored at room temperature. Observation of the appearance of the solution was conducted at 0, 1, 2, 4 and 6 hours. The amounts of cefoperazone sodium and sulbactam sodium were determined, and the results are shown below:

|  | Time (h) | | | | |
| --- | --- | --- | --- | --- | --- |
|  | 0 | 1 | 2 | 4 | 6 |
| Cefoperazone sodium | 98.42 | 97.39 | 97.46 | 94.70* | 93.02* |
| Sulbactam sodium | 92.44 | 91.27 | 90.78 | 88.38* | 86.86* |

*the solution turned slightly turbid,
**the solution turned turbid

Example 15

Pharmaceutical Composition of Cefoperazone Sodium, Sulbactam Sodium, Gentamicin Sulfate, Disodium EDTA, and Sodium Citrate Preparation Sodium citrate (0.20 g) was dissolved in 200 mL of injectable water, and the pH value was adjusted to 6.5 with citric acid/sodium hydroxide buffer. Cefoperazone sodium (4 g), sulbactam sodium (4 g), and sodium EDTA (1 mg) were then added, and the mixture was shaken. Gentamicin sulfate (160 mg/2 mL, parenteral solution) was added dropwise, and small amount of white floc has precipitated out. After 15 min of ultrasonication, the white floc had dissolved to give a clear solution. The solution was sealed and stored at room temperature. Observation of the appearance of the solution was conducted at 0, 1, 2, 4 and 6 hours, respectively. The amounts of cefoperazone sodium and sulbactam sodium in the solution were determined, and the results are shown below:

|  | Time (h) | | | | |
|---|---|---|---|---|---|
|  | 0 | 1 | 2 | 4 | 6 |
| Cefoperazone sodium | 101.7 | 96.06 | 95.72 | 97.32* | 69.95** |
| Sulbactam sodium | 99.50 | 96.28 | 102.5 | 95.78* | 70.74** |

*the solution turned slightly turbid,
**the solution turned turbid

Example 16

Pharmaceutical Composition of Cefoperazone Sodium, Tazobactam Sodium, Etimicin Sulfate, and Sodium Citrate Preparation Sodium citrate (0.20 g) was dissolved in 200 mL of injectable water, and the pH value was adjusted to 6.5 with citric acid/sodium hydroxide buffer. Cefoperazone sodium (4 g), tazobactam sodium (1 g), and sodium EDTA (1 mg) were then added, and the mixture was shaken. Freeze-dried injectable powder of etimicin sulfate (200 mg) was added. After 15 min of ultrasonication, a clear solution was obtained. The solution was sealed and stored at room temperature. Observation of the appearance of the solution was conducted at 0, 1, 2, 4, 6 and 8 hours. The amounts of cefoperazone sodium and tazobactam sodium were determined, and the results are shown below:

|  | Time (h) | | | | | |
|---|---|---|---|---|---|---|
|  | 0 | 1 | 2 | 4 | 6 | 8 |
| Cefoperazone sodium | 102.9 | 108.6 | 104.6 | 99.50 | 98.91 | 103.4 |
| tazobactam sodium | 98.77 | 108.2 | 110.8 | 97.39 | 106.3 | 106.3 |

Example 17

Pharmaceutical Composition of Mezlocillin Sodium, Sulbactam Sodium, Etimicin Sulfate, Disodium EDTA, and Sodium Citrate Preparation Sodium citrate (0.20 g) was dissolved in 200 mL of injectable water, and the pH value was adjusted to 6.5 with citric acid/sodium hydroxide buffer. Mezlocillin sodium (2 g), sulbactam sodium (1 g), and sodium EDTA (1 mg) were then added, and the mixture was shaken. Freeze-dried injectable powder of etimicin sulfate (200 mg) was added. After 15 min of ultrasonication, a clear solution was obtained. The solution was sealed and stored at room temperature. Observation of the appearance of the solution was conducted at 0, 1, 2, 4, 6 and 8 hours. The amounts of mezlocillin sodium, sulbactam sodium and etimicin sulfate in the mixture were determined, and the results are shown below:

|  | Time (h) | | | | | |
|---|---|---|---|---|---|---|
|  | 0 | 1 | 2 | 4 | 6 | 8 |
| Mezlocillin sodium | 116.6 | 94.83 | 91.86 | 91.96 | 91.52 | 98.56 |
| Sulbactam sodium | 114.3 | 95.83 | 93.75 | 93.78 | 95.65 | 101.0 |
| Etimicin sulfate | 100.1 | 100.4 | 99.31 | 99.56 | 99.61 | 99.25 |

Example 18

Pharmaceutical Composition of Mezlocillin Sodium, Sulbactam Sodium, Etimicin Sulfate, Disodium EDTA, and Sodium Citrate Preparation Sodium citrate (0.20 g) was dissolved in 200 mL of 2.5% injectable aqueous fructose solution, and the pH value was adjusted to 6.5 with citric acid/sodium hydroxide buffer. Mezlocillin sodium (2 g), sulbactam sodium (0.5 g), and sodium EDTA (1 mg) were added, and the mixture was shaken. Etimicin sulfate (200 mg) was added, and a small amount of white floc had precipitated out. After 15 min of ultrasonication, the floc was dissolved to give a clear solution. The solution was sealed and stored at room temperature. Observation of the appearance of the solution was conducted at 0, 1, 2, 4, 6 and 8 hours. The amounts of mezlocillin sodium, sulbactam sodium and etimicin sulfate in the mixture were determined, and the results are shown below:

|  | Time (h) | | | | | |
|---|---|---|---|---|---|---|
|  | 0 | 1 | 2 | 4 | 6 | 8 |
| Mezlocillin sodium | 96.48 | 95.90 | 71.70 | 91.78 | 93.08 | 97.69 |
| Sulbactam sodium | 98.07 | 98.13 | 72.96 | 95.16 | 99.65 | 104.9 |
| Etimicin | 100.1 | 100.6 | 99.79 | NA | NA | NA |

NA: undetermined content

Example 19

Pharmaceutical Composition of Cefoperazone Sodium, Sulbactam Sodium, Amikacin Sulfate, Disodium EDTA, and Sodium Citrate Preparation Sodium citrate (0.20 g) was dissolved in 200 mL of injectable water, and the pH value was adjusted to 6.75 with citric acid/sodium hydroxide buffer. Cefoperazone sodium (4 g), sulbactam sodium (1 g), and disodium EDTA (1 mg) were then added, and the mixture was shaken. A lyophilized injectable powder of amikacin sulfate (500 mg) was added, and a small amount of white floc had precipitated out. After 10 min of ultrasonication, the white floc had dissolved to give a clear solution. The solution was sealed and stored at room temperature. HIAC data at 1 and 20 hours were determined (see Table 1). Observation of the appearance of the solution was conducted at 0, 1, 2, 4, 6 and 8 hours, respectively. The amounts of cefoperazone sodium, sulbactam sodium and amikacin sulfate in the solution were determined, and the results are shown below:

|  | Time (h) | | | | | |
|---|---|---|---|---|---|---|
|  | 0 | 1 | 2 | 4 | 6 | 8 |
| Cefoperazone sodium | 95.91 | 97.01 | 95.94 | 95.86 | 95.41 | 95.22 |
| Sulbactam sodium | 108.8 | 109.6 | 111.7 | 115.9 | 120.7 | 125.6 |
| Amikacin | 99.91 | 99.50 | 98.88 | 99.45 | 98.56 | 99.36 |

Example 20

Pharmaceutical Composition of Cefoperazone Sodium, Sulbactam Sodium, Amikacin Sulfate, and Sodium Citrate Preparation Sodium citrate (0.20 g) was dissolved in 200 mL of injectable water, and the pH value was adjusted to 6.75 with citric acid/sodium hydroxide buffer. Cefoperazone sodium (4 g) and sulbactam sodium (1 g) were then added, and the mixture was shaken. A lyophilized injectable powder of amikacin sulfate (500 mg) was added, and a small amount of white floc had precipitated out. After 5 min of ultrasonication, the floc was dissolved to give a clear solution. The solution was sealed and stored at room temperature. HIAC data at 1 and 20 hour were determined (see Table 1). Observation of the appearance of the solution was conducted at 0, 1, 2, 4, 6 and 8 hours. The amounts of cefoperazone sodium, sulbactam sodium, and amikacin sulfate in the mixture were determined, and the results are shown below:

|  | Time (h) | | | | | |
|---|---|---|---|---|---|---|
|  | 0 | 1 | 2 | 4 | 6 | 8 |
| Cefoperazone sodium | 92.30 | 94.80 | 94.06 | 94.12 | 93.15 | 94.50 |
| Sulbactam sodium | 105.6 | 112.2 | 112.6 | 118.5 | 123.3 | 127.1 |
| Amikacin | 95.98 | 91.49 | 85.05 | 91.00 | 81.93 | 89.98 |

Example 21

Pharmaceutical Composition of Cefoperazone Sodium, Tazobactam Sodium, Gentamicin Sulfate, Disodium EDTA, and Sodium Citrate Preparation Sodium citrate (0.20 g) was dissolved in 200 mL of injectable water, and the pH value was adjusted to 6.75 with citric acid/sodium hydroxide buffer. Cefoperazone sodium (4 g), disodium EDTA (1 mg), and tazobactam sodium (1 g) were then added, and the mixture was shaken. Lyophilized injectable powder of gentamicin sulfate (160 mg) was added, and small amount of white floc had precipitated out. After 15 min of ultrasonication, the floc had dissolved to give a clear solution. The solution was sealed and stored at room temperature (22° C.). Observation of the appearance of the solution was conducted at 0, 1, 2, 4, 6 and 8 hours. The amounts of cefoperazone sodium, and tazobactam sodium in the solution were determined, and the results are shown below:

|  | Time (h) | | | | | |
|---|---|---|---|---|---|---|
|  | 0 | 1 | 2 | 4 | 6 | 8 |
| Cefoperazone sodium | 92.44 | 104.6 | 102.4 | 97.95* | 98.90* | 102.9* |
| Tazobactam sodium | 93.36 | 104.8 | 100.0 | 96.58* | 106.1* | 107.1* |

*the solution turned slightly turbid,
**the solution turned turbid

Example 22

Pharmaceutical Composition of Azlocillin Sodium, Sulbactam Sodium, Etimicin Sulfate, Disodium EDTA, and Sodium Citrate Preparation Sodium citrate (0.20 g) was dissolved in 200 mL of 2.5% injectable aqueous fructose solution, and the pH value was adjusted to 6.0 with citric acid/sodium hydroxide buffer. Azlocillin sodium (1.2 g), sulbactam sodium (0.3 g), and disodium EDTA (1 mg) were then added, and the mixture was shaken. Etimicin sulfate (200 mg) was added, and a small amount of white floc had precipitated out. After 5 min of ultrasonication, the floc had dissolved to give a clear solution. The solution was sealed and stored at room temperature. Observation of the appearance of the solution was conducted at 0, 1, 2, 4, 6 and 8 hours. The amounts of azlocillin sodium, sulbactam sodium, and etimicin sulfate in the solution were analyzed, and the results are shown below:

|  | Time (h) | | | | | |
|---|---|---|---|---|---|---|
|  | 0 | 1 | 2 | 4 | 6 | 8 |
| Azlocillin sodium | 92.40 | 98.91 | 104.0 | 98.91 | 99.03 | 85.02 |
| Sulbactam sodium | 101.4 | 107.6 | 101.3 | 104.4 | 104.4 | 91.39 |

Example 23

Pharmaceutical Composition of Azlocillin Sodium, Sulbactam Sodium, Etimicin Sulfate, Disodium EDTA, and Sodium Citrate Preparation Sodium citrate (0.20 g) was dissolved in 200 mL of 2.5% injectable aqueous fructose solution, and the pH value was adjusted to 6.75 with citric acid/sodium hydroxide buffer. Azlocillin sodium (2.4 g), sulbactam sodium (0.3 g), and disodium EDTA (1 mg) were then added, and the mixture was shaken. Etimicin sulfate (200 mg) was added, and a small amount of white floc had precipitated out. After 5 min of ultrasonication, the floc had dissolved to give a clear solution. The solution was sealed and stored at room temperature. Observation of the appearance of the solution was conducted at 0, 1, 2, 4, 6 and 8 hours. The amount of etimicin in the solution was determined, and the results are shown below:

|          | Time (h) |       |       |       |       |       |
|----------|----------|-------|-------|-------|-------|-------|
|          | 0        | 1     | 2     | 4     | 6     | 8     |
| Etimicin | 104.5    | 99.13 | 103.3 | 98.75 | 101.6 | 96.42 |

Example 24

Pharmaceutical Composition of Ceftriaxone Sodium, Sulbactam Sodium, Etimicin Sulfate, Disodium EDTA, and Sodium Citrate Preparation Sodium citrate (0.20 g) was dissolved in 200 mL of injectable water, and the pH value was adjusted to 6.75 with citric acid/sodium hydroxide buffer. Ceftriaxone sodium (2 g), sulbactam sodium (0.5 g), and disodium EDTA (1 mg) were then added, and the mixture was shaken. Etimicin sulfate (200 mg, lyophilized powder) was added, and small amount of white floc had precipitated out. After 5 min of ultrasonication, a clear solution was obtained. The solution was sealed and stored at room temperature. Observation of the appearance of the solution was conducted at 0, 1, 2, 4, 6, and 8 hours. The amounts of ceftriaxone sodium and sulbactam sodium in the solution were determined, and the results are shown below:

|                    | Time (h) |        |       |        |        |       |
|--------------------|----------|--------|-------|--------|--------|-------|
|                    | 0        | 1      | 2     | 4      | 6      | 8     |
| Ceftriaxone sodium | 110.2    | 117.6  | 119.4 | 111.5  | 113.4  | 120.0 |
| Sulbactam sodium   | 90.06    | 94.26  | 100.5 | 89.94  | 94.26  | 105.0 |

Example 25

Pharmaceutical Composition of Cefodizime Sodium, Sulbactam Sodium, Etimicin Sulfate, Disodium EDTA, and Sodium Citrate Preparation Sodium citrate (0.20 g) was dissolved in 200 mL of injectable water, and the pH value was adjusted to 6.75 with citric acid/sodium hydroxide buffer. Cefodizime sodium (2 g), sulbactam sodium (0.5 g), and disodium EDTA (1 mg) were added, and the mixture was shaken. Etimicin sulfate (200 mg, lyophilized powder) was then added, and a small amount of white floc precipitated out. After 5 min of ultrasonication, a clear solution was obtained. The solution was sealed and stored at room temperature. Observation of the appearance of the solution was conducted at 0, 1, 2, 4, 6 and 8 hours. The amounts of cefodizime sodium and sulbactam sodium were determined, and the results are shown below:

|                   | Time (h) |       |       |       |       |       |
|-------------------|----------|-------|-------|-------|-------|-------|
|                   | 0        | 1     | 2     | 4     | 6     | 8     |
| Cefodizime sodium | 100.9    | 104.6 | 100.1 | 81.34 | 103.7 | 102.2 |
| Sulbactam sodium  | 99.32    | 107.5 | 97.91 | 83.79 | 94.52 | 105.5 |

Example 26

Pharmaceutical Composition of Azlocillin Sodium, Sulbactam Sodium, Etimicin Sulfate, Disodium EDTA, and Sodium Citrate Preparation Sodium citrate (0.20 g) was dissolved in 200 mL of 2.5% injectable aqueous fructose solution, and the pH value was adjusted to 6.75 with citric acid/sodium hydroxide buffer. Azlocillin sodium (2.4 g), sulbactam sodium (0.3 g), and disodium EDTA (1 mg) were added, and the mixture was shaken. Etimicin sulfate (200 mg) was added, and a small amount of white floc had precipitated out. After 5 min of ultrasonication, the floc had dissolved to give a clear solution. The solution was sealed and stored at room temperature. Observation of the appearance of the solution was conducted at 0, 1, 2, 4, 6 and 8 hours. The amount of etimicin in the solution was determined, and the results are shown below:

|          | Time (h) |       |       |       |       |       |
|----------|----------|-------|-------|-------|-------|-------|
|          | 0        | 1     | 2     | 4     | 6     | 8     |
| Etimicin | 94.69    | 102.9 | 109.3 | 108.8 | 109.6 | 105.2 |

Example 27

HIAC Test

Light obscuration testing was performed for solution preparations prepared with some of the compositions described in the examples according to the method described in the United States Pharmacopeia (USP 788) using HIAC-3000 light obscuration detector. Results are shown in Table 1. Particle content is denoted by the number of particles per milliliter of solution. The value is an average of two measurements. Samples were tested at 1 hour and at 20 hours.

TABLE 1

| | HIAC test results | | | | | |
|---|---|---|---|---|---|---|
| | Aminoglycoside | | Number of particles (ppm) | | | |
| | antibiotics | Disodium | 1 hr | | 20 hrs | |
| Sample | (mg/mL) | EDTA (mg/mL) | 10 μm | 25 μm | 10 μm | 25 μm |
| Example 4 | G (0.4) | 0.0 | 49 | 2 | 464 | 8 |
| Example 5 | G (0.4) | 0.005 | 21 | 0 | 68 | 0 |

TABLE 1-continued

HIAC test results

| | Aminoglycoside antibiotics | Disodium | Number of particles (ppm) | | | |
|---|---|---|---|---|---|---|
| | | | 1 hr | | 20 hrs | |
| Sample | (mg/mL) | EDTA (mg/mL) | 10 μm | 25 μm | 10 μm | 25 μm |
| Example 19 | A (2.5) | 0.005 | 31 | 1 | 129 | 2 |
| Example 20 | A (2.5) | 0.0 | 86 | 2 | 1598 | 10 |

G: Gentamicin;
A: Amikacin

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

The invention claimed is:

1. A pharmaceutical composition comprising: at least one β-lactam antibiotic selected from cefoperazone, ceftriaxone, cefodizime, mezlocillin, azlocillin, or a pharmaceutically acceptable salt or hydrate thereof, at least one ion-chelating agent, at least one buffer component having an effective pH range of between 6.0 and 6.75, and at least one aminoglycoside antibiotic selected from etimicin, gentamicin, amikacin, or a pharmaceutically acceptable salt thereof; wherein the pharmaceutical composition forms a clear and transparent solution without turbidity or precipitate, and the efficacy of the β-lactam antibiotic and the aminoglycoside antibiotic in the solution is maintained for at least 8 hours.

2. The pharmaceutical composition of claim 1, wherein said ion-chelating agent is ethylenediamine tetraacetic acid (EDTA), diethylenetriaminepentaacetic acid (DTPA), hydroxyethylethylenediaminetriacetic acid (HEDTA), or a pharmaceutically acceptable salt or hydrate thereof.

3. The pharmaceutical composition of claim 1, wherein said buffer component is citric acid/citrate, phosphoric acid/phosphate, acetic acid/acetate, arginine, carbonic acid/carbonate, or tris/HCl.

4. The pharmaceutical composition of claim 1, further comprising at least one β-lactamase inhibitor, wherein said β-lactamase inhibitor is clavulanic acid, sulbactam, or tazobactam, or a pharmaceutically acceptable salt or hydrate thereof.

5. The pharmaceutical composition of claim 1, provided in a unit dose formulation comprising between 10 mg and 5 g of said aminoglycoside antibiotic.

6. The pharmaceutical composition of claim 1, provided in a unit dose formulation comprising between 0.1 g and 5 g of said β-lactam antibiotic, between 0.1 mg and 500 mg of said ion-chelating agent, and between 0.01 g and 5 g of said buffer component.

7. The pharmaceutical composition of claim 4, provided in a unit dose formulation comprising between 0.1 g and 5 g of said β-lactam antibiotic, between 0.1 mg and 500 mg of said ion-chelating agent, between 0.1 g and 5 g of said β-lactamase inhibitor, and between 0.01 g and 5 g of said buffer component.

8. The pharmaceutical composition of claim 7 comprising:
(a) between 0.1 g and 5 g of cefoperazone, cefodizime, mezlocillin, azlocillin, ceftriaxone, or a pharmaceutically acceptable salt or hydrate thereof;
(b) between 0.1 g and 5 g of sulbactam sodium, clavulanate potassium, or tazobactam sodium;
(c) between 0.01 g and 5 g of sodium citrate; and
(d) between 0.1 mg and 500 mg of EDTA disodium.

9. The pharmaceutical composition of claim 6, comprising:
(a) between 0.1 g and 5 g of cefoperazone, cefodizime, mezlocillin, azlocillin, ceftriaxone, or a pharmaceutically acceptable salt or hydrate thereof;
(b) between 0.01 g and 5 g of sodium citrate; and
(c) between 0.1 mg and 500 mg of EDTA disodium.

10. The pharmaceutical composition of claim 1, comprising further at least one iso-osmotic component, wherein said iso-osmotic component is glucose or sodium chloride.

11. The pharmaceutical composition of claim 4, comprising further at least one iso-osmotic component, wherein said iso-osmotic component is glucose or sodium chloride.

12. The pharmaceutical composition of claim 1, provided as an injectable powder, freeze-dried injectable powder, parenteral solution, eye drops, nose drops, ear drops, inhalant, genital duct drops, wash, or solution for external use.

13. A method for preparing the pharmaceutical composition of claim 1 in a form of freeze-dried injectable powder, the method comprising the steps of:
(a) dissolving a β-lactam antibiotic, a β-lactamase inhibitor, disodium EDTA, and other components of the pharmaceutical composition in injectable water, in 2.5% injectable fructose aqueous solution, or in 5% normal saline; and adjusting the pH value to between 6 and 6.75;
(b) dividing solution obtained in step (a) into unit doses, each unit dose being placed in an individual container; placing the containers in a freeze-drier; and adjusting the temperature of the freeze drier to about minus 35° C.;
(c) evacuating the atmosphere in the freeze drier to below 40 Pa;
(d) adjusting the temperature in the freeze drier to between 3 and 5° C.;
(e) removing water completely under the above-mentioned conditions;
(f) adjusting the temperature of the freeze drier to between 40 and 50° C., and drying freeze-dried injectable powder obtained in step (e); and
(g) charging nitrogen into the freeze drier, sealing the containers with sterile seal-capping, and storing the containers below 5° C. in the dark.

14. Process for preparation of the pharmaceutical composition of claim 1, wherein said β-lactam antibiotic, buffer, and ion-chelating agent are mixed in a form of injectable powder to form a mixture; and when said mixture is formulated as an injectable solution, it is mixed in a container with a solution of said aminolycoside antibiotic.

15. Process for preparation of the pharmaceutical composition of claim 1, wherein said β-lactam antibiotic and ion-chelating agent are mixed in a form of injectable powder to form a mixture; and when said mixture is formulated as an injectable solution, it is mixed in a container with a solution of said aminolycoside antibiotic and said buffer component.

16. Process for preparation of the pharmaceutical composition of claim 6, wherein said β-lactam antibiotic, β-lactamase inhibitor, buffer, and ion-chelating agent are mixed in a form of injectable powder to form a mixture; and when said mixture is formulated as an injectable solution, it is mixed in a container with a solution of said aminolycoside antibiotic.

17. Process for preparation of the pharmaceutical composition of claim 6, wherein said β-lactam antibiotic, β-lactamase inhibitor and ion-chelating agent are mixed in a form of injectable powder to form a mixture; and when said mixture is formulated as an injectable solution, it is mixed in a container with a solution of said aminolycoside antibiotic and said buffer component.

18. A pharmaceutical composition comprising: at least one β-lactam antibiotic selected from cefoperazone, ceftriaxone, cefodizime, mezlocillin, azlocillin, or a pharmaceutically acceptable salt thereof, at least one ion-chelating agent, at least one buffer component having an effective pH range of between 6.0 and 6.75, and at least one aminoglycoside antibiotic selected from etimicin, gentamicin, or a pharmaceutically acceptable salt thereof; wherein the pharmaceutical composition forms a clear and transparent solution without turbidity or precipitate, and the efficacy of the β-lactam antibiotic and the aminoglycoside antibiotic in the solution is maintained for at least 8 hours.

19. A pharmaceutical composition comprising: at least one β-lactam antibiotic selected from cefodizime, mezlocillin, azlocillin, or a pharmaceutically acceptable salt or hydrate thereof, at least one ion-chelating agent, at least one buffer component having an effective pH range of between 6.0 and 6.75, and at least one aminoglycoside antibiotic selected from etimicin, gentamicin, or a pharmaceutically acceptable salt thereof; wherein the pharmaceutical composition forms a clear and transparent solution without turbidity or precipitate, and the efficacy of the β-lactam antibiotic and the aminoglycoside antibiotic in the solution is maintained for at least 8 hours.

* * * * *